United States Patent [19]

Kosaka

[11] Patent Number: 5,159,642
[45] Date of Patent: Oct. 27, 1992

[54] PARTICLE IMAGE ANALYZING APPARATUS

[75] Inventor: Tokihiro Kosaka, Hyogo, Japan

[73] Assignee: TOA Medical Electronics Co., Ltd., Kobe, Japan

[21] Appl. No.: 728,731

[22] Filed: Jul. 11, 1991

[30] Foreign Application Priority Data

Jul. 13, 1990 [JP] Japan ................... 2-185794
Jul. 13, 1990 [JP] Japan ................... 2-185795

[51] Int. Cl.⁵ ............................................. G06K 9/00
[52] U.S. Cl. .................................. 382/6; 356/23; 356/39
[58] Field of Search .............. 382/6, 1; 356/39, 23; 350/431; 364/413.25, 413.13

[56] References Cited

U.S. PATENT DOCUMENTS

| | | | |
|---|---|---|---|
| 4,070,113 | 7/1978 | Frazer et al. | 356/39 |
| 4,325,706 | 4/1982 | Gershman et al. | 356/39 |
| 4,338,024 | 7/1982 | Bolz et al. | 382/6 |
| 4,786,165 | 11/1988 | Yamamoto et al. | 382/6 |
| 5,007,732 | 4/1991 | Ohki et al. | 356/39 |

Primary Examiner—David K. Moore
Assistant Examiner—Yon Jung
Attorney, Agent, or Firm—Pearne, Gordon, McCoy & Granger

[57] ABSTRACT

A particle image analyzer includes a first light source for applying strobe light to a sample solution flowing through a flow cell, first image pick-up means for taking a still picture of a particle in the sample solution irradiated by the first light source, a second light source for constantly irradiating the sample solution in the flow cell, and second image pick-up means for picking up an image of the sample solution in the flow cell irradiated by the second light source. When a particle is detected from the image pick-up data from the second image pick-up means, the first light source is flashed, based upon detection of the particle, in a predetermined image pick-up interval of the first image pick-up means.

21 Claims, 17 Drawing Sheets

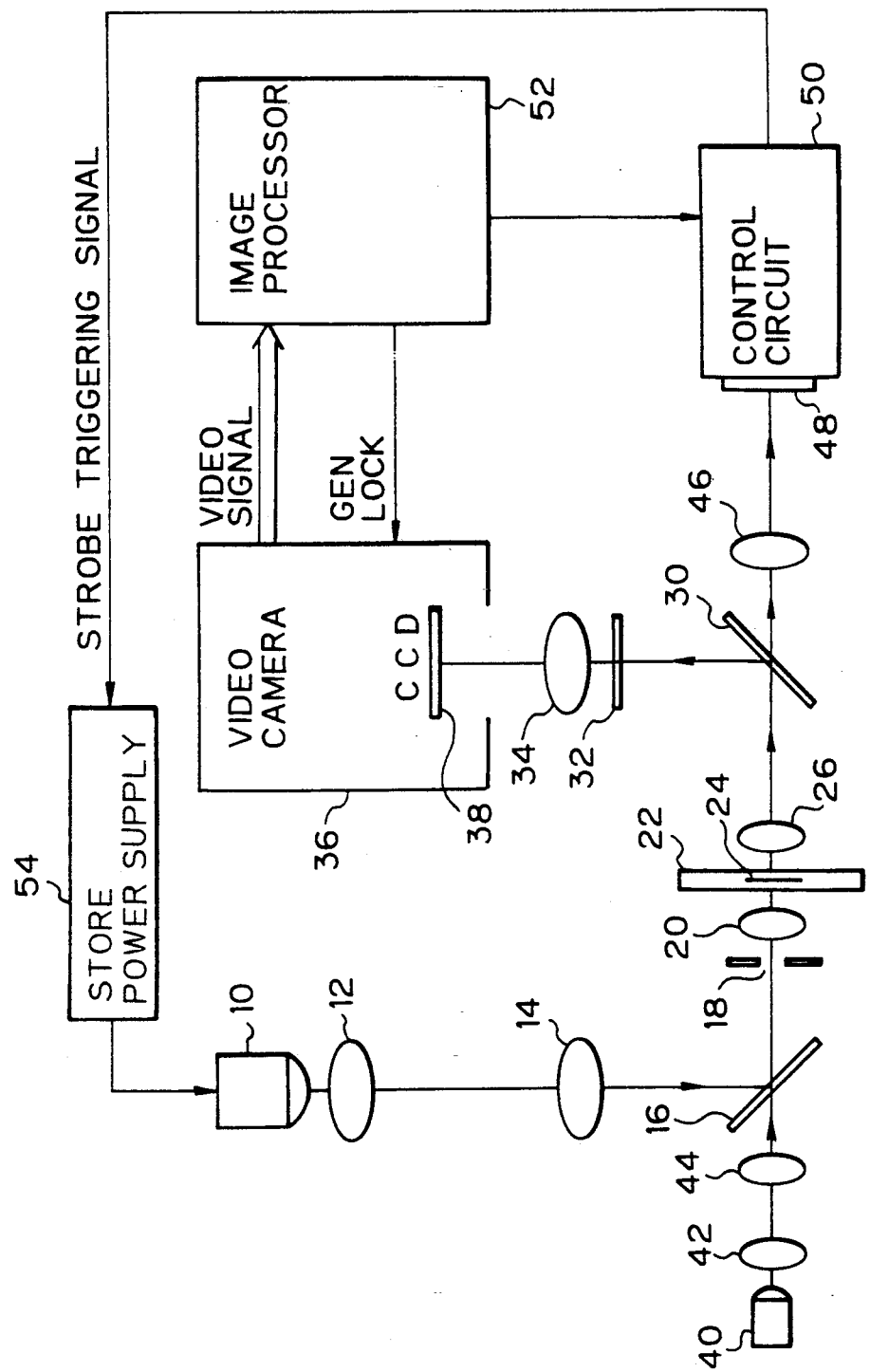

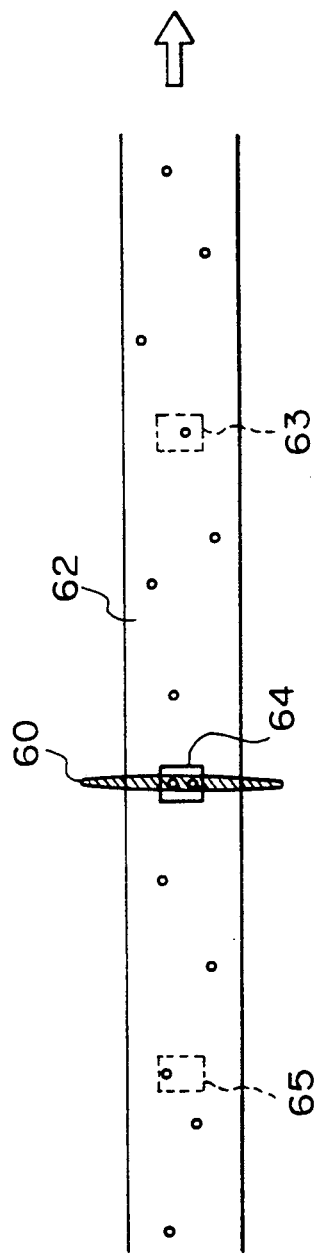

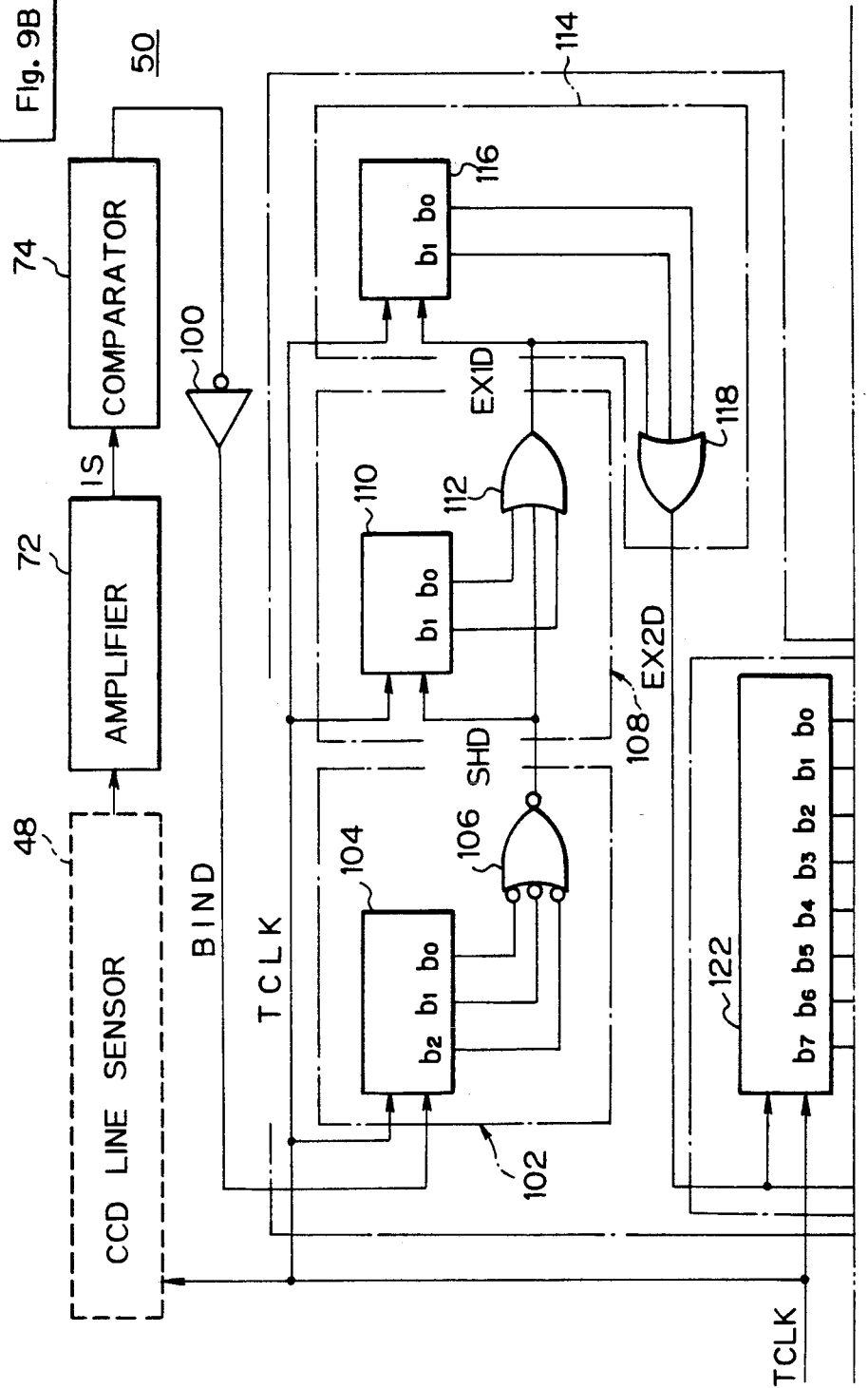

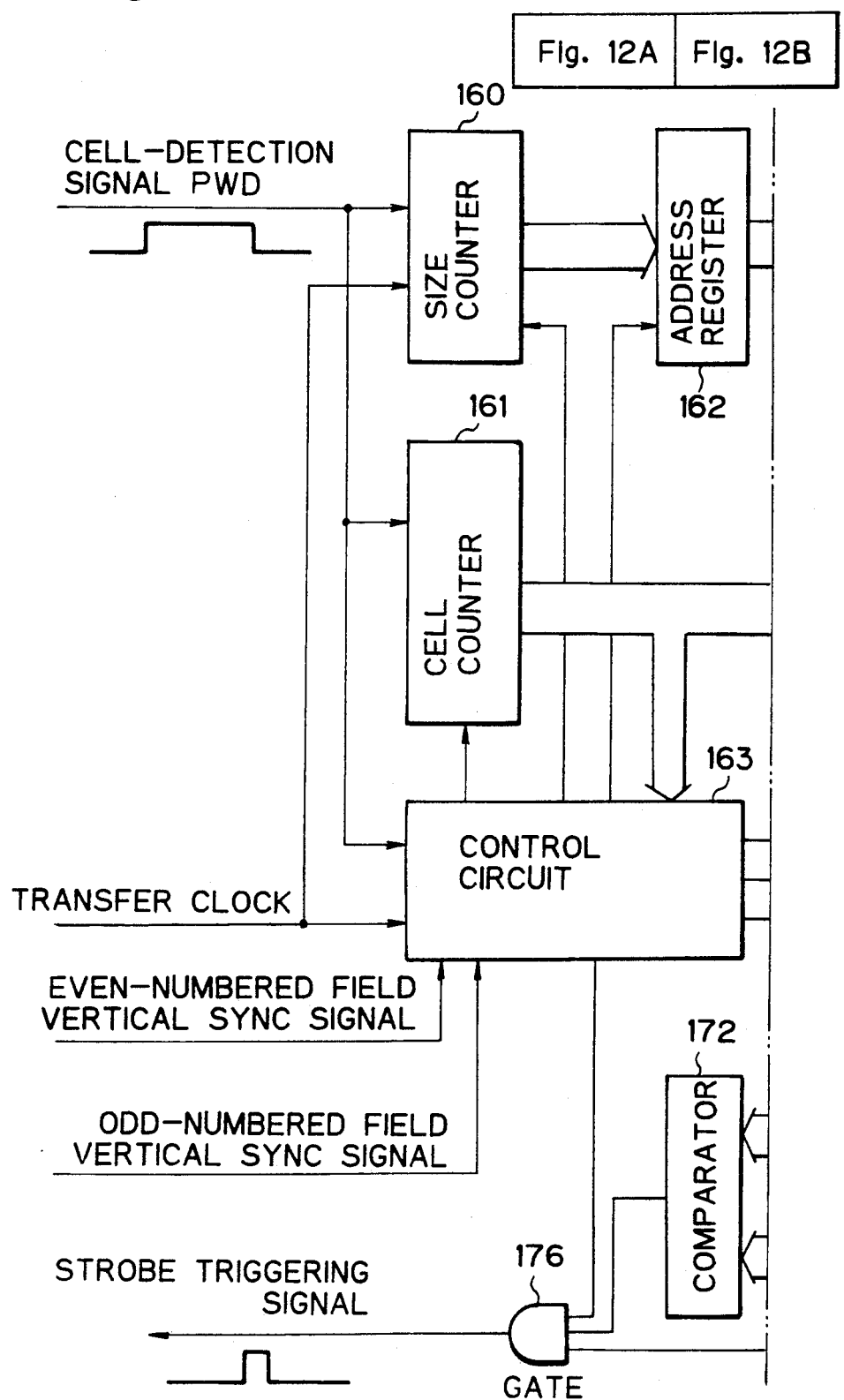

PARTICLE IMAGE ANALYZING APPARATUS

BACKGROUND OF THE INVENTION

1. Field of the Invention

This invention relates to an apparatus for forming a sample solution such as blood or urine into a flat sheathed flow, irradiating the flat flow of the sample solution with strobe light to obtain a still picture, and employing image processing to perform analysis such as classification and enumeration of particle components contained in the sample solution. More particularly, the invention relates to a particle image analyzing apparatus adapted to constantly monitor an image pick-up area and irradiate the particles in the sample solution flow with strobe light when they reach the image pick-up area, thereby making it possible to acquire an image of the particle components in an efficient manner even if the sample has a low particle content.

2. Description of the Prior Art

When the particle components contained in a sample of blood or urine taken from a living body are to be examined, the conventional practice is to prepare a sample by smearing the sample on a glass slide and observing the slide under a microscope to classify or enumerate the particle components. However, the conventional method is laborious and lacking in accuracy. Accordingly, in order to reduce the labor involved in examination and to improve accuracy, automatic analyzing apparatus have been developed, a specific example of which is disclosed in the specifications of Japanese Patent Application Laid-Open (KOKAI) No. 57-500995 and U.S. Pat. No. 4,338,024. The disclosed apparatus uses a strobe light to irradiate a sample solution sheathed in sheathing liquid and formed into a very flat flow, acquires a still picture by means of a video camera and subjects the picture to image processing to classify and/or enumerate material components contained in the sample. An automatic urinalysis apparatus to which this art is applied is already available on the market.

FIG. 15 is a block diagram showing the construction of the conventional apparatus of the kind described above. The apparatus includes an image processor 200 which produces a strobe triggering signal at fixed intervals to fire a strobe 202 at a regular time interval. The emitted strobe light is made to irradiate a sample solution, which flows through a flat passageway 208 in a flow cell 206, by an optical system 204 comprising lenses and other elements. The sample solution, which travels in a direction perpendicular to the plane of the drawing, flows in a broad width vertically of the drawing but in a small width horizontally thereof within the flat passageway 208. Light which has passed through the flow cell 206 has its image formed on a CCD light-receiving surface 214 of a video camera 212 by an optical system 210. The video camera 212 produces a video signal output in synch with a generator-lock signal from the image processor 200, and the video signal is subjected to image processing within the image processor 200. The strobe 202 is powered by a strobe power supply 216.

FIG. 16 is an enlarged view of a portion of the sample-solution flow as seen from the image pick-up side. Numeral 220 denotes the flat flow of the sample solution, in which particle components 222 are contained. The sample solution flows from left to right in FIG. 17, which is a perspective view of the image pick-up area. Numeral 224 denotes a portion of the sample-solution flow whose image is picked up by the video camera 212. In FIG. 16, numeral 226 denotes a portion of the sample-solution flow imaged just prior to portion 224, and numeral 228 denotes a portion of the sample-solution flow to be imaged following portion 224.

Ordinarily, the image pick-up operation performed by a video camera is such that one frame has a duration of 1/30 of a second. If the sample is irradiated with light every 1/30 of a second and the total measurement time is 45 seconds, then 1350 image frames can be acquired. However, if the sample solution has a low particle-component content, particle images will not necessarily appear in all of the frames. For example, assume that the sample is blood and that leukocytes are to be analyzed. In order to perform leukocyte analysis, the blood sample used is one in which the red blood cells have been subjected to hemolytic disruption and the leukocytes have been stained.

Now assume that a sample obtained by subjecting blood having a leukocyte content of 5000 cells/$\mu$l to the aforesaid pretreatment and finally diluted by ten times, namely a blood sample having a leukocyte content of 500 cells/$\mu$l, is passed through a flow cell and analyzed. Assume also that the image pick-up area is a square each of whose sides has a length of 150 $\mu$m, and that the thickness of the flat sheathed flow is 8 $\mu$m (in which case the volume of the image pick-up area will be 150 $\mu$m $\times$ 150 $\mu$m $\times$ 8 $\mu$m = $1.8 \times 10^{-4}$ $\mu$l).

As mentioned above, FIG. 17 is a perspective view of the image pick-up area. Numeral 230 denotes a leukocyte. When the leukocyte count per imaged frame is determined under the aforementioned conditions, the figure obtained is 500 cells/$\mu$l $\times$ $1.8 \times 10^{-4}$ $\mu$l = 0.09 cells. In other words, only one leukocyte appears in 11 imaged frames. This means that even if 1350 frames are obtained, as mentioned above, the number of frames in which leukocytes appear will be 1/11 of the total number of frames, or about 120 frames, according to simple calculation. In order to increase the number of frames in which leukocytes appear, three methods are conceivable: (a) lower the dilution rate of the sample (i.e., raise the concentration); (b) shorten the image pick-up cycle; and (c) enlarge the image pick-up area (volume).

Method (a) is disadvantageous in that the hemolysis of the red blood cells may be inadequate and the amount of blood necessary may need to be increased. With method (b), a special video camera capable of performing photography at 100 or more frames per second can be used, but such a camera is very expensive. Furthermore, it is necessary to raise the speed of image processing as well. Another problem is that since the irradiation cycle of the strobe is shortened, the quantity of light emitted can become erratic and the life time of the strobe may be shortened. When the image pick-up area is enlarged (i.e., when the magnification is reduced) according to method (c), the size of the cell image becomes smaller in relative terms. In addition, when the thickness of the float sheathed flow is increased, there is an increase in the number of cells which do not appear in focus, and the end result is a decline in cell-image resolution.

Thus, cell images cannot be obtained efficiently using the conventional method in which strobe light is emitted every 1/30 of a second to effect imaging.

In order to obtain cell images more efficiently, an effective expedient would be to irradiate a cell with the strobe light to obtain its image only when the cell arrives at the image pick-up area, and suspend photography when there are no cells in the image pick-up area. Examples of devices that could achieve this are an electrical-resistance-type detector comprising micropores and a pair of electrodes, and an optical detector comprising light-emitting and light-receiving elements. With such an arrangement, the presence of a cell would be detected by the detector. However, there is no assurance that a cell which has passed by the detector will always pass through the image pick-up area. The sample solution flows in a broad transverse spread in the proximity of the image pick-up area, and hence there are cases where cells miss the image pick-up area during their passage through the flow cell. In addition, the length of time from the moment a cell passes the detector until it reaches the image pick-up area tends to differ depending upon a variety of conditions. For this reason, cells cannot always be photographed at a correct timing.

SUMMARY OF THE INVENTION

In view of the foregoing, an object of the present invention is to provide a particle image analyzing apparatus whereby the images of particle components can be acquired efficiently at all times even if the sample has a low particle-component content.

(1) According to the present invention in a first aspect thereof, the foregoing object is attained by providing a particle image analyzing apparatus in which a sample solution containing particle components such as cells is formed into a very flat stream sheathed by a sheathing liquid and passed through a flat flow path of a flow cell, irradiating means and image pick-up means (image capturing means) are arranged on opposite sides of the flow cell, a still picture of the sample solution is taken and the particle components are subjected to analysis such as classification and enumeration by image processing applied to the still picture, characterized by provision of a first light source and first image pick-up means for picking up (capturing) the still picture, and of a second light source, second image pick-up means and control circuit for detecting particles which flow through a first image pick-up zone (image capturing zone).

A second image pick-up zone, which is formed in part of the flat sample flow by the second image pick-up means, is formed within the first image pick-up zone formed in part of the flat sample flow by the first image pick-up means.

The second image pick-up means is a line sensor whose pixels are arrayed in one dimension, and the second image pick-up zone (an image pick-up line) is formed so as to cross the flow of the sample.

The second light source emits light at all times (continuously), and the emitted light has its image formed on the second image pick-up means via the second image pick-up zone.

The control circuit receives a signal from the second image pick-up means, senses arrival of a particle component and produces a trigger signal to fire a strobe serving as the first light source. In response to the trigger signal, the first light source emits light for a short period of time, and the light has its image formed on the first image pick-up via the first image pick-up zone.

The light from the first light source includes visible light, while the light from the second light source is, for example, infrared light and includes no visible light.

Light-selecting means (light-separating means) is provided in front of the first and second image pick-up means and selects (separates) light so as to apply only visible light to the first image pick-up means and infrared light to the second image pick-up means.

In a preferred embodiment, the control circuit comprises an amplifier connected to the second image pick-up means, a comparator connected to the amplifier, a particle detecting circuit connected to the comparator, and a strobe controller connected to the particle detecting circuit.

The strobe controller is adapted to output the trigger signal when a particle-detection signal from the particle detecting circuit provides to the strobe controller during an interval (period) in which an image is capable of being picked up by the first image pick-up means.

(2) According to the present invention in a second aspect thereof, the particle detecting circuit of the first aspect in a preferred embodiment comprises a shift register for converting a serial binary signal from the comparator into a parallel signal, and a particle discriminator, to which the parallel signal from the shift register is applied, for performing particle discrimination.

In the first aspect of the invention, a cylindrical lens preferably is provided between the second light source and the flow cell. In addition, the sample undergoing measurement is blood that has been subjected to hemolytic and staining treatments, and the particles of interest are leukocytes. Alternatively, the sample undergoing measurement is urine that has been subjected to a staining treatment, and the particles of interest are material components contained in the urine.

(3) According to the present invention in a third aspect thereof, a compressing circuit (shrinking circuit) connected to the comparator, a first expanding circuit connected to the compressing circuit, and a second expanding circuit connected to the first expanding circuit preferably are provided between the comparator and the particle analyzing circuit.

The meaning of "compression (shrink)" as used here is as follows: In a case where binary signals representing a pixel of interest of the second image pick-up means and the pixels adjacent to the pixel of interest on either side indicate portions of a particle, the binary signal representing the pixel of interest is adopted as being that indicative of the particle. In other cases, this binary signal is adopted as being indicative of the background. The meaning of "expansion" is as follows: In a case where binary signals representing a pixel of interest and at least one of the pixels adjacent to the pixel of interest on either side indicate portions of a particle, the binary signal representing the pixel of interest is adopted as being that indicative of the particle. In other cases, this binary signal is adopted as being indicative of the background.

(4) According to the present invention in a fourth aspect thereof, the apparatus of the third aspect can be additionally provided with a particle counting circuit comprising a selecting circuit connected to the particle detecting circuit, and a counter connected to the selecting circuit. Upon continuously receiving particle-detection signals over plural scanning periods (scanning cycles) of the second image pick-up means, the selecting circuit outputs, as a signal for counting particles, only a particle-detection signal of the initial scanning period. The counter counts the signal outputted by the selecting circuit.

(5) According to the present invention in a fifth aspect thereof, the apparatus of the third aspect can be additionally provided with a circuit for forming a pulse-width signal that reflects particle size, this circuit comprising one line memory or a plurality of line memories for temporarily storing a binary signal, a condition detecting circuit for detecting whether a specific condition holds upon receiving an input signal which arrives via the line memory and an input signal which does not arrive via the line memory, and a circuit for obtaining the particle-detection signal by taking the OR, under the specific condition, of the signals continuously received over the aforementioned plural scans.

(6) According to the present invention in a sixth aspect thereof, the apparatus of the fifth aspect can be additionally provided with a size counter for measuring the pulse width of the particle-detection signal, a histogram memory connected to the size counter for storing the incidence of pulse widths whenever a pulse width is measured, and a control circuit for controlling the size counter and the histogram memory.

(7) According to the present invention in a seventh aspect thereof, the apparatus of the fifth aspect can be additionally provided with a size counter for measuring the pulse width of the particle-detection signal, first and second size registers for storing upper- and lower-limit values of pulse width, a first comparator to which upper-limit value data from the first size register is inputted as comparison data and pulse-width data from the size counter is inputted as data to be judged, a second comparator to which lower-limit value data from the first size register is inputted as comparison data and pulse-width data from the size counter is inputted as data to be judged, a control circuit for controlling the size counter, the size registers and the comparators, and a gate to which outputs from the first and second comparators and an output from the control circuit are inputted. When the pulse width of the particle-detection signal is within a range bounded by the lower-limit value and the upper-limit value, the gate outputs a strobe triggering signal.

(8) According to the present invention in an eighth aspect thereof, the apparatus of the seventh aspect is capable of being provided with a histogram memory.

The operation of the present invention will be described in brief.

(1) The second light source emits light at all times and irradiates the second image pick-up zone. Light which has passed through this zone reaches the second image pick-up means via the light selecting means. The signal from the second image pick-up means is sent to the control circuit, and it is determined in real-time whether a particle has arrived at the second image pick-up zone. If arrival of a particle component is sensed, the control circuit outputs a trigger signal in response to which the first light source emits light for a short period of time. This light from the first light source irradiates the particle for a short period of time. The second image pick-up zone is formed within the first image pick-up zone. The arrangement is such that the infrared light from the second light source is kept from reaching the first image pick-up means by the light selecting means. As a consequence, only the light from the first light source is selected and reaches the first image pick-up means, whereby a still picture of the particle is taken.

The signal from the second image pick-up means that has entered the control circuit is amplified by the amplifier and converted into a binary value by the comparator. The binarized signal enters the particle detecting circuit, where it is determined from the state of the binary signal whether the signal is one indicative of a particle or not. If it is found that the signal is the result of a particle, then the particle-detection signal is produced as an output. This signal enters the strobe controller. If the present point in time is in an interval during which the first image pick-up means is capable of picking up an image, the strobe controller outputs the trigger signal for firing the first light source into light emission.

(2) The serial binary signal is converted into a parallel signal by the shift register, and the particle discriminator determines whether the signal is indicative of a particle. If the result of the determination is that a particle is present, the particle-detection signal is produced as an output.

(3) The binary signal is applied to the compressing circuit, which eliminates unnecessary signal components indicative of contaminants, noise, etc. Only necessary portions of the signal are expanded by the first expanding circuit, whereby the signal is restored to its original state. A signal which more accurately expresses fill-in of the interior of a particle and the size of the cell image is obtained by the second expanding circuit.

(4) In a case where the same particle is scanned a plurality of times by the second image pick-up means, a plurality of particle-detection signals corresponding to the consecutive plurality of scans are obtained with regard to one particle. Accordingly, if particle-detection signals are obtained in consecutive scans, the selecting circuit outputs only the initial particle-detection signal as the signal for counting particles. This signal is counted by the counter to obtain the particle count.

(5) In a case where a train of plural binary signals is obtained in consecutive scans of one particle, the OR (the logical sum) of these signals is taken, whereby there can be obtained a signal having a pulse width more correctly reflecting particle diameter. However, one particle-detection signal cannot be obtained with regard to one particle merely by taking the OR. Accordingly, the arrangement adopted is such that the condition detecting circuit detects when a specific condition holds, at which time the OR of the aforementioned signals is taken, thereby obtaining one particle-detection signal for one particle.

(6) The pulse widths of particle-detection signals are individually measured and converted into data by the size counter. The items of resulting pulse-width data are sent to the histogram memory, where the pulse-width data is set as the memory address and frequency data corresponding to the address is incremented in sequential fashion. By designating addresses of the histogram memory, the frequency data is read out sequentially so that a histogram relating to the pulse width of the particle-detection signal can be obtained. Information such as the particle count also can be obtained if such a histogram is used.

(7) The upper-limit value of pulse width is stored in the first size register, and the lower-limit value of pulse width is stored in the second size register. The pulse-width data of the particle-detection signal obtained by the size counter is compared with the upper-limit value by means of the first counter, and the latter outputs a signal if the pulse width is less than the upper-limit value. The pulse-width data is compared with the lower-limit value by means of the second counter, which outputs a signal if the pulse width is greater than the lower-limit value. Meanwhile, when the first image pick-up means is in an interval during which it is capable of image pick-up, the control circuit produces a signal indicative of this fact. The above-mentioned signals are tied together by an AND gate, whereby it is possible to produce the trigger signal for firing the first light source only when a particle whose size is in the range bounded by the upper- and lower-limit values is detected in an interval during which the first image pick-up means is capable of image pick-up.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a block diagram illustrating the principal components of a first embodiment of a particle image analyzing apparatus according to the present invention;

FIG. 2 is an enlarged view showing part of the flow of a sample solution as seen from the image pick-up side in FIG. 1;

FIG. 9A-B is a block diagram illustrating the principal components of a second embodiment of a control circuit according to the present invention;

FIGS. 11A-B and 12A-B are block diagrams illustrating the principal components of a third embodiment of the present invention;

DETAILED DESCRIPTION OF THE PREFERRED EMBODIMENTS

Figure 4:
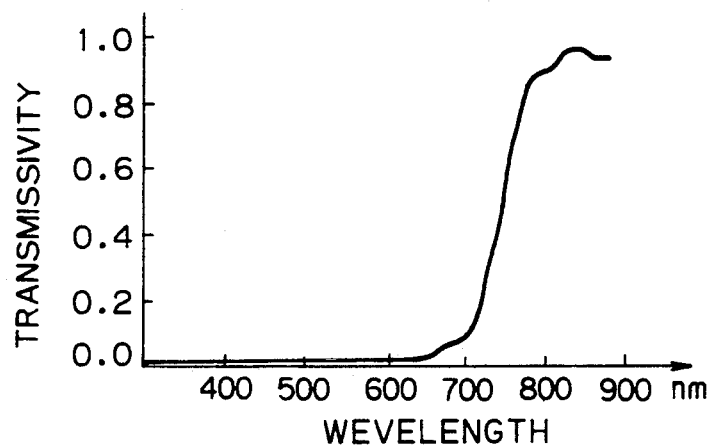
FIG. 4 is a diagram showing an example of the characteristic of a dichroic mirror.

Preferred embodiments of the present invention will now be described in detail with reference to the drawings.

FIG. 1 is a block diagram illustrating a first embodiment of a particle image analyzing apparatus according to the present invention. The apparatus of FIG. 1 includes a flow cell 22 for forming a blood sample, which has been subjected to treatments for hemolysis and staining, into an extremely flat flow sheated by a sheathing liquid. The sample solution flows perpendicular to the plane of the drawing from the front side toward the back side thereof. The flow cell 22 has a flow path 24 whose dimension in the direction parallel to the optic axis of irradiation (the horizontal direction in FIG. 1) is on the order of 100-200 $\mu$m, and whose dimension in the direction perpendicular to the optic axis of irradiation (namely the vertical direction in FIG. 1) is on the order of several millimeters. Accordingly, the sample solution which flows through the flat flow path 24 also is formed into a flat stream that is very thin (e.g., 5-10 $\mu$m) in the direction of the optic axis of irradiation and very broad (e.g., several hundred microns) in the direction perpendicular to the optic axis of irradiation.

The apparatus of FIG. 1 further includes a first light source 10 used in taking a still picture of a cell, and first image pick-up means 36. More specifically, the first light source 10 is a strobe, and the first image pick-up means 36 is a color video camera.

Further, the apparatus has a second light source 40 and second image pick-up means 48 for performing constant monitoring in order to determine whether a cell (particle) has arrived at the image pick-up area for the still-picture photography mentioned above. More specifically, the second light source 40 is a semiconductor laser which emits infrared light at a wavelength of 780-830 nm, and the second image pick-up means 48 is a CCD line sensor whose pixels are arrayed in a single line.

Light emitted by the semiconductor laser 40 is collimated by a collimator lens 42, and the collimated light is made to strongly converge in the direction of sample flow by a cylindrical lens 44. As a result, the laser light, designated at numeral 60 in FIG. 2, is made to irradiate a first image pick-up zone 64 narrowly in the flow direction of the sample soultion, shown at numeral 62, and broadly in the direction perpendicular to the flow direction. FIG. 2 is an enlarged view of the sample-solution flow as seen from the image pick-up side in FIG. 1.

Figure 3:
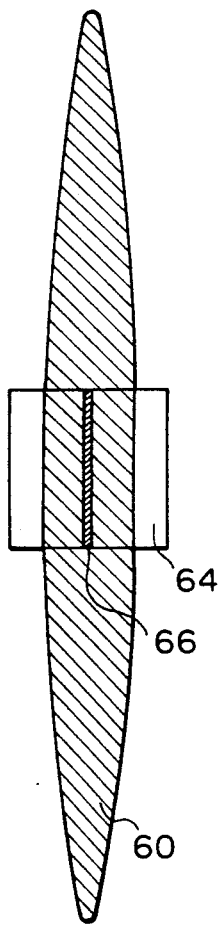
FIG. 3 is an enlarged view showing part of a first image pick-up zone.

FIG. 3 is an enlarged view showing the first image pick-up zone.

In FIG. 3, numeral 64 denotes the first image pick-up zone in which an image is picked up by the first image pick-up means 36, and numeral 66 denotes the second image pick-up zone (indicated by the hatching slanting downward from upper right to lower left) in which an image is picked up by the second image pick-up means 48. The first image pick-up area 64 is two-dimensional in form, one example being a square each of whose sides is 150 $\mu$m in length. The second image pick-up zone 66 is formed one dimensionally so as to cut across the first image pick-up zone 64 at right angles to the flow of the sample solution. The second image pick-up zone 66 has a width of about 1 $\mu$m and a length of 150 $\mu$m. Hereinafter, the first image pick-up zone shall be referred to as an "image pick-up area" and the second image pick-up zone as an "image pick-up line". An irradiation area 60 irradiated by the second light source 40, which is indicated by the hatching slanting downward from upper left to lower right, spreads widely over the image pick-up line 66. Though the irradiation area irradiated by the first light source 10 is not shown, it spreads widely over the image pick-up area 64 as a matter of course.

By thus narrowing the light from the second light source 40 down to a slender, elongated beam, the light can be concentrated into the image pick-up line efficiently even if the slight source is a semiconductor laser having small output, and the S/N ratio at the light-receiving portion can be improved. In addition, since any change in the quantity of light in the direction of the image pick-up line also can be made small.

The apparatus of FIG. 1 includes a visible-light reflector 16, a condensor lens 20 and a dichroic mirror 30 of the type that allows infrared light to pass therethrough. An example of the characteristic (angle of incidence: 45°) of the dichroic mirror 30 is shown in FIG. 4.

Infrared light which has passed through the flow cell 22 has its image formed on a line image sensor 48 via an objective lens 26, the dichroic mirror 30 and a projecting lens 46. The image of the image pick-up line 66 shown in FIG. 3 is formed on the line sensor 48. Voltages conforming to the quantity of light stored pixel by pixel are successively outputted by the line image sensor 48 and enter a control circuit 50. The output of the line image sensor 48 is amplified by the control circuit 50, in which the amplified signal is compared with a threshold level and thus converted into a binary value so that the control circuit may determine whether a particle has arrived. When arrival of a particle has been detected, the control circuit 50 outputs a strobe triggering signal which causes the strobe 10 to emit light.

Since the transmitted light has its image formed on the line image sensor 48, the portion in which the cell appears has a reduced quantity of light, and the binary signals of the pixels corresponding to this portion attain a LOW level.

Figure 7:
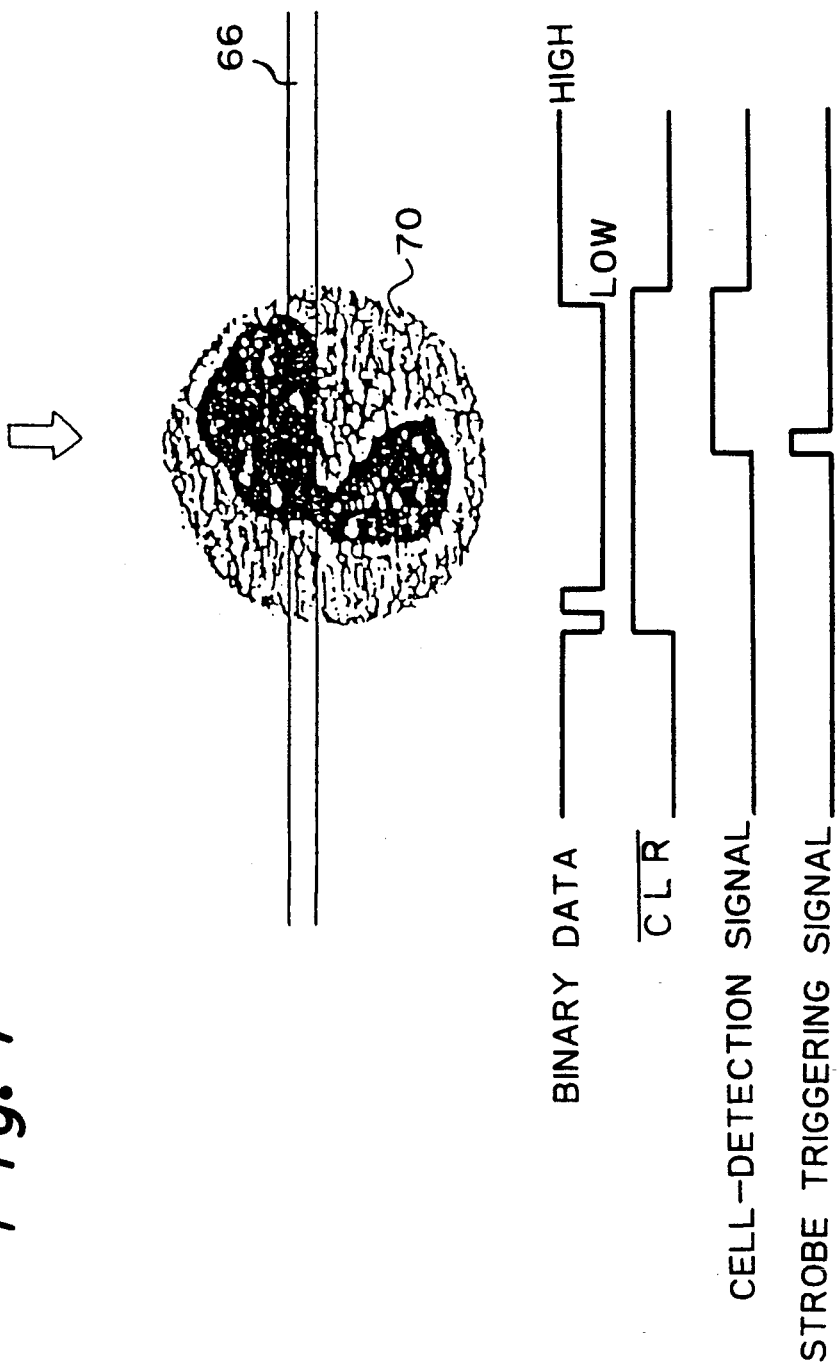
FIG. 7 is a diagram showing an image formed by an image sensor.

This situation is illustrated in FIG. 7, in which numeral 70 denotes a leukocyte. In order that cells which pass through the image pick-up area may be monitored by the line image sensor 48 at all times without any cells being missed, the distance that a cell of interest travels within the scanning period of the line image sensor 48 must be made smaller than the size of the cell. In other words, it is necessary that the traveling speed of the cell be made less than a certain value.

Let the image pick-up range per pixel in the line direction of the line image sensor 48 be 1 $\mu$m, and let the size of a leukocyte be 15 $\mu$m. In a simple case, the binary signal will go LOW 15 times in succession. In actuality, however, leukocytes differ in size and staining depending upon the type of leukocyte, and the sample solution contains red blood-cell membranes (ghosts) compressed by hemolysis. Therefore, it is required that leukocytes be judged upon taking these factors into account. A specific example of leukocyte judgement will be described below. The judgements made in the control circuit 50 are executed in real-time. When arrival of a leukocyte has been determined, the control circuit 50 outputs the trigger signal that causes the light source 10 to emit strobe light. The light source 10 is powered by a power supply 54.

Figure 5:
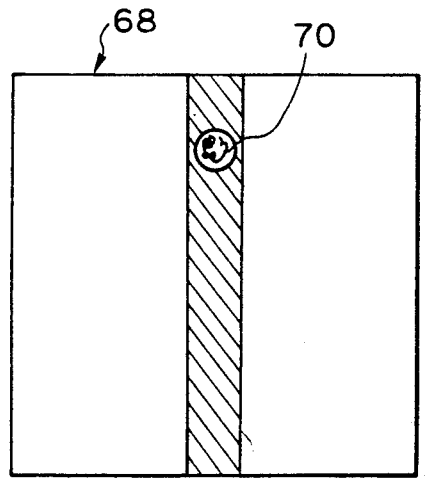
FIG. 5 is a diagram showing an imaged frame in a video camera.

The strobe light from the light source 10 is acted upon by a collimator lens 12 and a collector lens 14 and then reflected by the dichroic mirror 16. The reflected light is condensed by a diaphragm 18 and the condenser lens 20 to irradiate the image pick-up area. The light transmitted through the image pick-up area passes through the objective lens 26 and is reflected by the dichroic mirror 30. The resulting reflected light is acted upon by an infrared filter 32 and is then condensed by a projecting lens 34 so that an image is formed on a light-receiving surface 38 within the video camera 36. Since the image pick-up line has been formed so as to cross the image pick-up area, the position at which the leukocyte 70 appears in the photographic frame 68 when the leukocyte has been detected and photographed by the video camera 36 is limited to the hatched zone as shown in FIG. 5. This makes it unnecessary to process the entire area of the frame when image processing is carried out. As a result, the invention provides the collateral effects of simpler processing software or hardware and higher processing speed. (The prior-art method is deficient in these respects because the location at which the cells appear is random, thus making more comprehensive processing necessary.) The video signal from the video camera 36 is synchronized by a genlock signal from an image processor 52, and the image signal picked up by the camera is sent to the image processor 52 to be subjected to a variety of image processing.

Described next will be the control circuit 50 which determines whether a cell has arrived at the image pick-up area and performs control for strobe-light emission.

Figure 6:
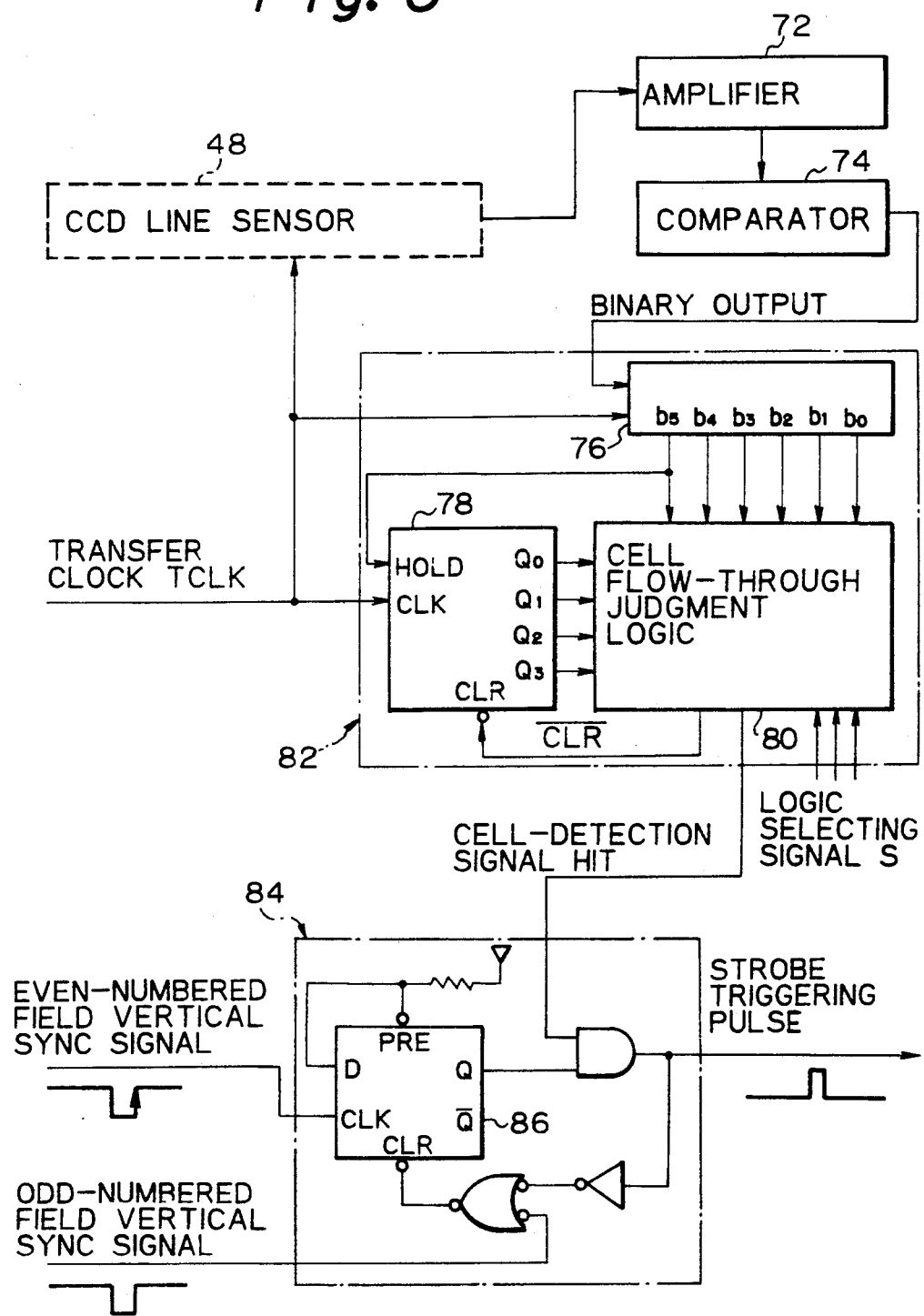
FIG. 6 is a block diagram showing the details of a control circuit in FIG. 1.

FIG. 6 is a circuit diagram showing the details of the control circuit 50.

The light whose image has been formed on each pixel of the line image sensor (a CCD image sensor) is photoelectrically converted, and the resulting electric charge is accumulated for a period of time equivalent to the scanning period of the line image sensor 48. The electric charge accumulated for each pixel is transferred in synchronism with a transfer clock, and a voltage conforming to each charge quantity is delivered by the line image sensor 48 as an output. The output voltage is amplified by an amplifier 72, and the amplified voltage is compared with an appropriate threshold level by a comparator 74, whereby the voltage is converted into a binary or two-valued signal indicative of HIGH (hereinafter referred to simply as "H") or LOW (hereinafter referred to simply as "L"). An appropriate threshold level is one so decided that a particle image and a background image can be distinguished from each other.

FIG. 7 illustrates the manner in which the leukocyte 70 flows in from upper part of the diagram and arrives at the image pick-up line 66. The binary signal assumes the "L" level as a result of the leukocyte crossing the image pick-up line.

With reference again to FIG. 6, a binary signal which attains the "H" level with regard to a pixel at a portion on which a cell image is not formed and which assumes the "L" level with regard to a pixel at a portion on which a cell image is formed is sent from the comparator 74 to a cell detecting circuit 82 which, if a cell has been detected, outputs a cell-detection signal HIT. The cell-detection signal HIT is applied to a strobe control circuit 84. If the prevailing interval is one in which image pick-up is possible, the strobe control circuit 84 outputs the strobe triggering signal, which causes the light source 10 to emit strobe light.

The cell detecting circuit 82 comprises a shift register 76, a cell discriminator 80 and a counter 78. The binary signals enter the shift register 76 sequentially to be shifted bit by bit in synch with the transfer clock so as to obtain parallel outputs $b_5$–$b_0$ (bit $b_5$ is the latest binary signal, and the bits $b_4$, $b_3$, $b_2$, $b_1$, $b_0$ are successively older). Depending upon the state of the bit $b_5$, the counter 78 counts up the transfer clock or holds without counting up the transfer clock. The counter 78 holds when the bit $b_5$ is "H" and counts up when the bit $b_5$ is "L". Since the binary signals are synchronized with the transfer clock, pixels for which the binary signal is "L" are counted by the counter 78, and the value of the count is outputted as four-bit data $Q_3$, $Q_2$, $Q_1$, $Q_0$, which enters the cell discriminator 80. When the count is greater than a predetermined value, the cell discriminator 80 outputs the cell-detection signal HIT. By way of example, the following logic would be used in the cell discriminator 80 in order to output the cell-detection signal HIT at a count of 9 or above:

$$HIT = (Q_3 \times Q_0) + (Q_3 \times Q_1) + (Q_3 \times Q_2)$$

where $Q_3$ is the most significant bit.

The counter 78 is cleared by a clearing signal produced based on the parallel data $b_5-b_0$. The counter 78 continues counting until the clearing signal is applied thereto. When the output of a pixel corresponding to the background is being outputted, the clearing signal assumes the "L" level, thereby clearing the counter 78. When the output of a pixel corresponding to a portion of cell is being outputted, the clearing signal attains the "H" level and the counter 78 performs counting.

The clearing signal is formed using the following logic, which serves as an example:

$$\overline{CLR} = (b_5 \times \overline{b_4}) + (b_5 \times b_4 \times b_3 \times \overline{b_2})$$

In this logic, $(b_5 \times b_4)$ is for making the clearing signal active ("L") in a case where two consecutive pixels output signals indicative of background, and the bits $(b_5 \times \overline{b_4} \times b_3 \times \overline{b_2})$ are for making the clearing signal "L" in a case where four consecutive pixels output "H", "L", "H", "L".

Stated in simple terms, when a leukocyte arrives at the image pick-up line, the pixels corresponding to this portion output signals indicative of the cell. In other words, a plurality of consecutive pixels output cell signals. Therefore, it will suffice to count the number of binary signals which consecutively attain the "L" level. In actuality, however, there are also cases where the output of a pixel corresponding to a cell does not always assume the "L" level owing to the stained state of the cell nucleus, granule and cytoplasm (see FIG. 7). Accordingly, it is required that the aforementioned threshold level and cell judgment logic be optimized depending upon the type, size and stained condition of the cell of interest. In this embodiment, an example is illustrated in which a counter is used in the cell discriminator. However, rather than using a counter, an arrangement can be adopted in which the parallel output bits of the shift register are increased in number and a judgment is made upon inputting this parallel data. Other embodiments also are conceivable in accordance with the particular specifications.

A selection signal S which enters the cell discriminator 80 at the lower right in FIG. 6 is for selecting optimum judgment conditions if cells of interest are believed to be of several types or if a fine adjustment of judgment conditions is required. The content of the selection signal S is designated from the image processor 52. Further, the logic of the cell discriminator 80 can be realized with ease by a single programmable-array logic IC (PAL) available on the market. The cell detecting circuit 82 also can be incorporated within a single IC along with the shift register and counter.

Next, in response to the cell-detection signal from the cell discriminator 80, the trigger signal for causing an emission of strobe light is produced. In a case where the video camera is of the type in which a screen of one frame is formed from an odd-numbered field screen and an even-numbered field screen, it is necessary to use a frame-storing-type video camera.

If a field-storing-type video camera were to be used, a picture of one field would have to be adopted as one picture. This would have the vertical resolution and result in lower resolution.

In the case where the frame-storing video camera is employed, the strobe must be made to emit light during an even-numbered field interval.

Figure 8:
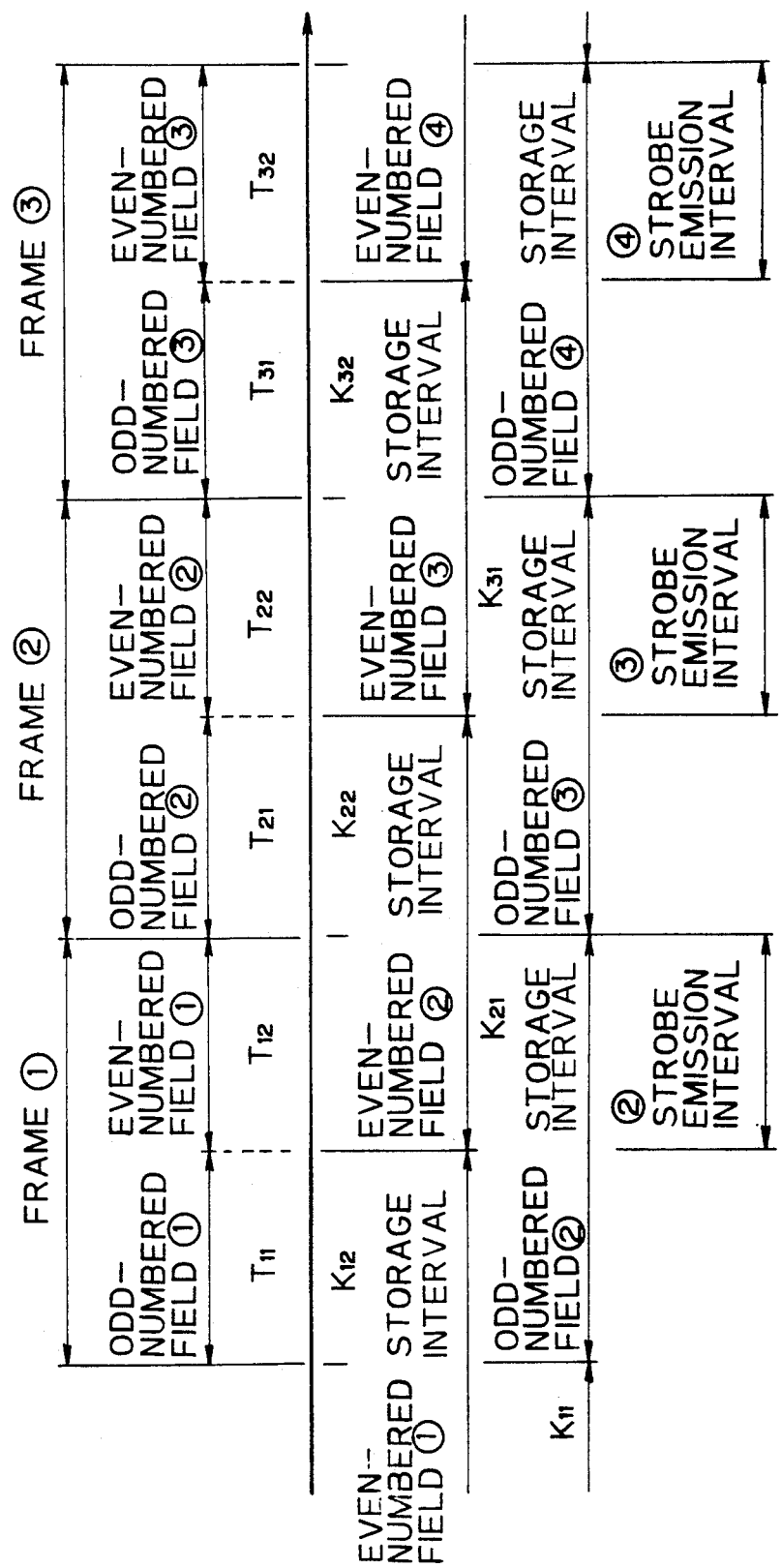
FIG. 8 is a diagram for describing strobe emission timing.

FIG. 8 is a timing chart for describing the timing of strobe emission. Electric charge stored in a storage interval (period) $K_{21}$ of an odd-numbered field ② is outputted in an interval (period) $T_{21}$ of the odd-numbered field ②, and electric charge stored in a storage interval (period) $K_{22}$ of an even-numbered field ② is outputted in an interval (period) $T_{22}$ of the even-numbered field ②. Accordingly, if the strobe light is emitted in an interval (period) $T_{12}$ in which the intervals $K_{21}$ and $K_{22}$ overlap, the odd-numbered field picture of the resulting still picture is outputted in the interval $T_{21}$ of the odd-numbered field ②, and the even-numbered field picture is outputted in the interval $T_{22}$ of the even-numbered field ②. A picture of one frame is thus formed. Similarly, if the strobe light is emitted during interval (period) $T_{22}$, the resulting still picture is outputted in an interval (period) $T_{31}$ of an odd-numbered field ③ and in an interval (period) $T_{32}$ of an even-numbered field ③.

However, if the strobe light were to be emitted in the odd-numbered field intervals (period) $T_{11}$ and $T_{21}$, the odd-numbered field picture of a frame ② would become one obtained by irradiation performed in interval $T_{11}$ of an odd-numbered field ①, and the even-numbered field picture of the frame ② would become one obtained by irradiation performed in interval (period) $T_{21}$ of an odd-numbered field ②. Thus, a picture of the correct frame ② could be constructed.

Further, if the strobe light were to be emitted in the interval $T_{12}$ of the even-numbered field ① and in the interval $T_{21}$ of the odd-numbered field ②, the picture of the even-numbered field of frame ② would be double-exposed.

Thus, in a case where it is arranged so that a picture of one frame is formed from a picture of an odd-numbered frame and a picture of an even-numbered frame, there are intervals in which the strobe light can and cannot be emitted. It is required that the strobe light be emitted in an interval where such an emission is possible.

To this end, it is necessary to inhibit a strobe-light emission in odd-numbered field intervals (periods). In addition, it is necessary to inhibit two or more light emissions in one even-numbered field interval (period).

FIG. 6 illustrates the strobe control circuit 84 for producing the strobe triggering signal in a case where the cell-detection signal is detected in a state where correct image pick-up is possible. The strobe control circuit 84 includes a D-type flip-flop 86 whose Q output attains the "H" level in response to the leading edge of a vertical-field synchronizing signal generated at the start of an even-numbered field. The strobe triggering signal is obtained by taking the AND of this Q-output signal and the cell-detection signal ("H"). The strobe triggering signal is fed back to the clear terminal of the flip-flop 86, and therefore the flip-flop is cleared, and the Q output reverts to the "L" level, when the strobe triggering signal is produced. This means that the strobe triggering signal is not produced even if the cell-detection signal is obtained again in the even-numbered field interval.

The flip-flop 86 is cleared also by a vertical synchronizing signal at the start of an odd-numbered field interval. As a result, the Q output assumes the "L" level and the strobe triggering signal is not produced.

The Q output of the flip-flop 86 attains the "H" level in response to the next even-numbered field vertical synchronizing signal.

The usefulness of the present invention when practiced will now be described.

A probability density function of the particle interval of particles which flow through a sheathed flow generally is expressed by the following equation:

$$f_\beta(t) = \beta e^{-\beta t} \quad (1)$$

where t represents the particle interval, and $\beta$ represents a constant decided depending upon various conditions.

If Eq. (1) is normalized using an average value $t_{av}$ of the particle interval, a probability density function f(t) can be expressed as follows:

$$f(t) = e^{-t} \quad (2)$$

This makes calculations easier to handle. Hereinafter, t shall represent a ratio with respect to $t_{av}$.

Letting $F(t_i)$ represent the probability that the particle interval will exceed $t_i$, we have $$F(t_i) = \int_{t_i}^{\infty} f(t)dt \quad (3)$$
$$= \int_{t_i}^{\infty} e^{-t}dt = e^{-t_i}$$

The probability that a particle (cell) will pass through the image pick-up area within the period of one field is obtained from the equation above.

Let $t_c$ represent a value obtained by dividing the average interval of particles by the period of the field. We then have the following:

(a) When $t_c = 3$ holds, namely when the average interval of particles is ⅓ of the period 1/60 sec of one field, the image pick-up probability is 95.0%, obtained by approximation.

(b) When $t_c = 2$ holds, namely when the average interval of particles is ½ of the period of one field, the image pick-up probability is 86.5%.

(c) When $t_c = 1$ holds, namely when the average interval of particles is the same as the period of one field, the image pick-up probability is 63.2%.

A concrete example will now be illustrated in which $t_c$ is obtained and the image pick-up probability of a leukocyte calculated. The conditions are as follows:

sample: blood containing leukocytes in an amount of 5000 cells/$\mu$l sample for measurement: sample obtained by subjecting the above-mentioned blood sample to hemolytic and staining treatments and then diluting the solution ten times (resulting solution contains leukocytes in an amount of 500 cells/$\mu$l image pick-up capacity: 150 $\mu$m × 150 $\mu$m × 8 $\mu$m = $1.8 \times 10^{-4}$ $\mu$l line sensor scanning period: 33 $\mu$sec flat-sheath flow velocity: 10 $\mu$m/33 $\mu$sec = 5 mm/field, where the period of one field is 1/60 sec The scanning period of the line sensor, which is decided by such factors as the response of the line sensor and the required light storage times, is made as short as possible. It is required that the flow velocity of the sheath flow, namely the traveling velocity of the particles, be set in such a manner that a particle will not travel a distance greater than its size within the scanning period of the line sensor. The reason for this is that the line sensor would be incapable of detecting a cell clearly if the amount of cell movement were too great.

Based upon the foregoing conditions, the flow rate of a sample through the image pick-up area in an even-numbered field interval (1/60 sec) is $$150\mu m \times 8\mu m \times 5mm = 6 \times 10^{-3} \mu l$$

The number of leukocytes which pass through the image pick-up area in an even-numbered field interval is, on average, $$500 \text{ cells}/\mu l \times 6 \times 10^{-3} \mu l = 3 \text{ cells}$$

Accordingly, the average value of the interval between neighboring particles is ⅓ of the field interval, and $t_c = 3$. In other words, the image pick-up probability is 95.0%. This value is a major improvement in comparison with the probability of 9% in the conventional method of image pick-up performed merely at a fixed period. On the assumption that measurement is performed for 45 sec, about 1350 leukocyte images will be picked up.

An additional advantage of the present invention is that a high image pick-up probability can be maintained even if the image pick-up area (volume) is made small. For instance, even if the image pick-up area is made 1/4.5 of 100 $\mu$m × 100 $\mu$m × 4 $\mu$m = $4 \times 10^{-5}$ $\mu$l in the foregoing example, the volume of the sample solution which passes through the image pick-up area in an even-numbered field interval (1/60 sec) will be $$100\mu m \times 4\mu m \times 5mm = 2 \times 10^{-3} \mu l$$

and the average number of leukocytes which pass through the image pick-up area in an even-numbered field interval will be $$500 \text{ cells}/\mu l \times 2 \times 10^{-3} \mu l = 1 \text{ cell/field}$$

Further, $t_c = 1$. Therefore, the image pick-up probability will be about 63.2%. With the conventional method, the image pick-up probability would fall significantly to 2% of the original 1/4.5.

By reducing the size of the image pick-up area, cell images which are comparatively large, or which are brought into better focus by reducing the thickness of the sample-solution flow, can be obtained. This makes possible highly reliable analysis.

Image pick-up of cells according to the present invention is not performed at a fixed period but is so adapted that cells are photographed in intentional or deliberate fashion. This means that even if cell images are counted in an imaged frame, the leukocyte count per unit volume cannot be obtained correctly. However, the leukocyte count per unit volume can be obtained based upon the results of cell determination made by the line sensor, namely by counting the number of cell-detection signals outputted by the cell detecting circuit 82 in FIG. 6. By investigating whether a photographed cell is a leukocyte, obtaining the ratio of leukocytes in the cell image obtained and multiplying this by the number of cells which pass through the image pick-up area, a more correct leukocyte count can be calculated. In the above-mentioned example, about 8000 leukocytes can be counted in a measurement time of 45 sec. Thus, it is possible for the apparatus to perform also the function of a blood-cell counter. With the conventional method, the number of leukocytes capable of being photographed is 100 in this time period, and therefore the method cannot be applied in a blood-cell counter.

The present embodiment has been illustrated in a case where blood is used as the sample. However, it goes without saying that samples capable of being analyzed by the apparatus of the invention are not limited to blood. The apparatus can be used also when the sample is urine and particle components (cells such as blood cells, blood cast, etc.) contained in the urine are analyzed.

Urine contains particle components of markedly different sizes. In order to analyze a urine sample efficiently and accurately, therefore, it is necessary to photograph the particle components while changing over magnification during measurement. For more details, see the specification of Japanese Patent Application No. 1-243107 filed by the present applicant.

A case will now be described in which the invention is applied solely to a high-magnification mode.

What can be said first of all is that the cell-image pick-up probability is raised by a wide margin. The effect is particularly pronounced in the high-magnification mode. The fact that the cell-image pick-up probability is raised can be regarded substantially as representing an increase in the urine sample analyzed, and accuracy of analysis is improved.

In the high-magnification mode, measurement time is shortened slightly by an amount corresponding to the increase in the quantity of urine analyzed. Measurement time in the low-magnification mode is lengthened so that a limited measurement time can be utilized effectively.

A second embodiment of the present invention will now be described. In comparison with the first embodiment, the second embodiment is characterized in that the control circuit 50 is additionally provided with a correcting processing function and a cell counting function.

Figure 9B:
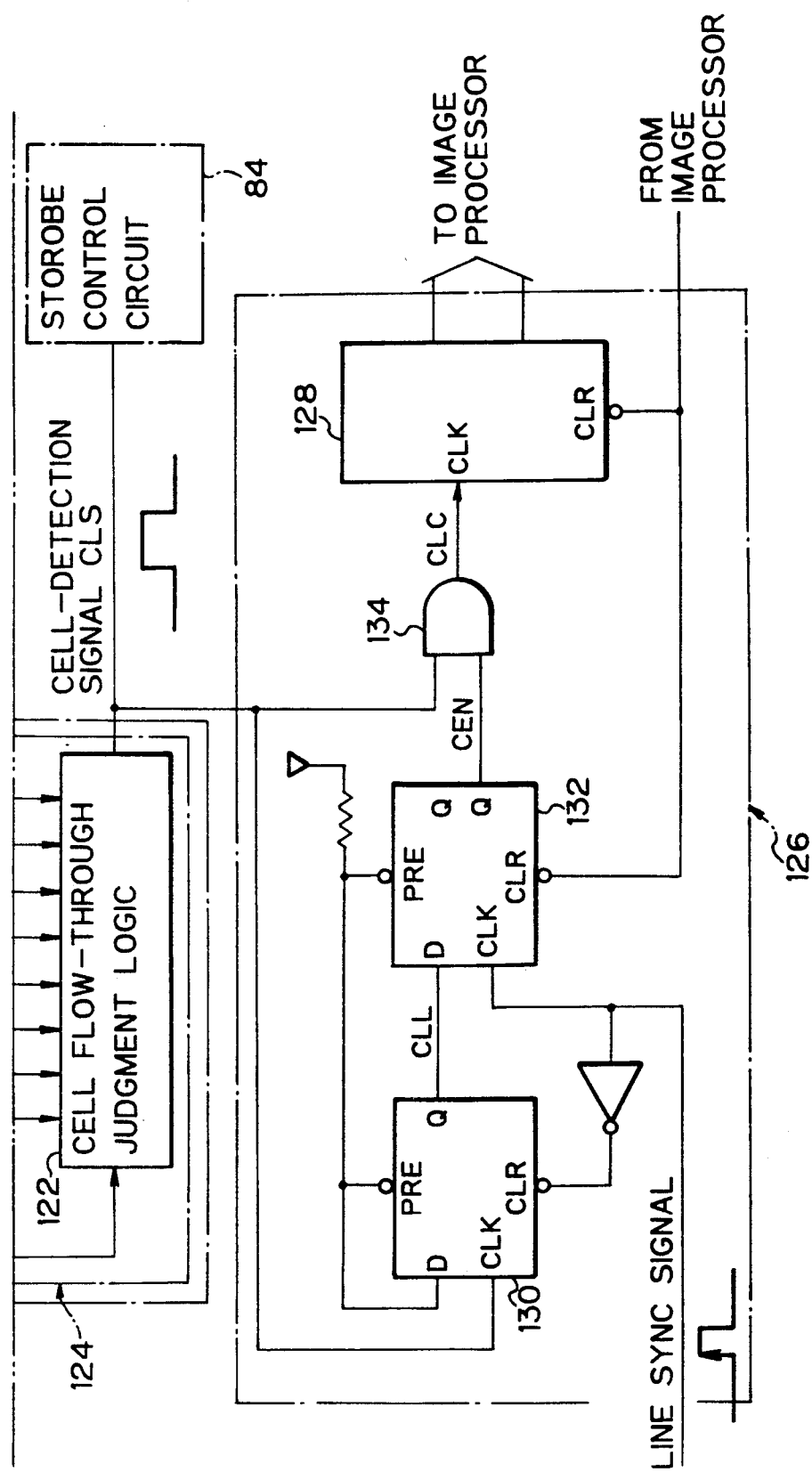

FIG. 9 is a block diagram illustrating the principal components of the control circuit 50 according to the second embodiment of the present invention. In FIG. 9, numeral numbers identical with those in FIG. 6 designated like or corresponding portions.

Figure 10:
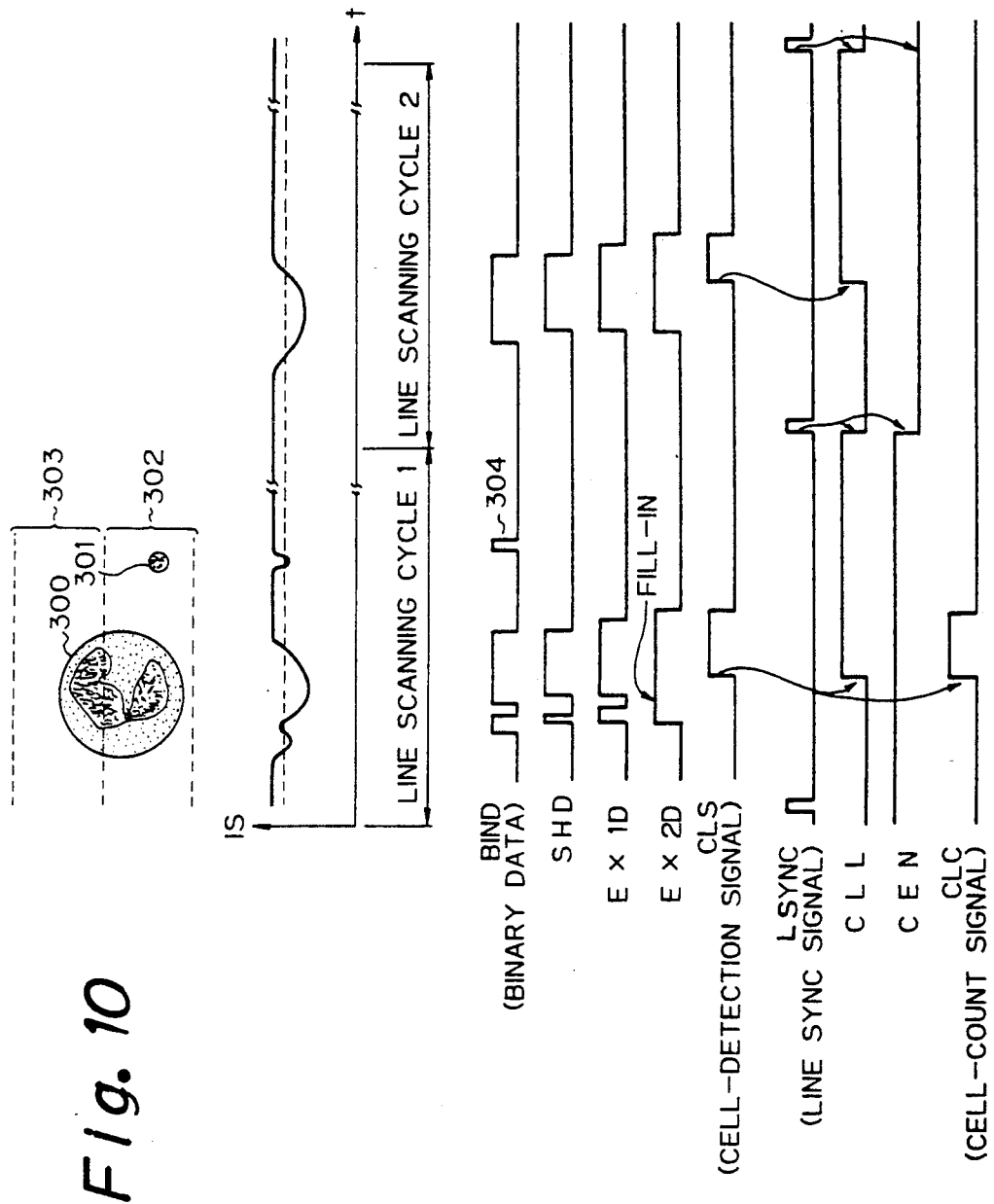
FIG. 10 is an operation timing chart according to the second embodiment of the present invention.

FIG. 10 is a timing chart showing various waveforms associated with FIG. 9. Symbols identical with those in FIG. 9 designate like waveforms.

The timing chart of FIG. 10 covers an instance where an image contains a dust particle 301 in addition to a cell 300. In FIG. 10, numeral 302 denotes an image which crosses the line sensor during a line-scanning cycle 1, and 303 denotes an image crossing the line sensor during a line-scanning cycle 2.

The operation which characterized the second embodiment thus constructed will now be described.

Though an operation similar to that of the first embodiment, a voltage corresponding to the quantity of light accumulated pixel by pixel in one scanning period is outputted by the line image sensor 48 in synch with a transfer clock (TCLK). This signal is amplified (to a signal IS) by the amplifier 72 before being binarized by the comparator 74. The resulting binary signal is inverted (to a signal BIND) by an inverter 100. The binary signal BIND outputted by the inverter 100 attains the "H" level with respect to a portion of the sample that is a cell, as shown in FIG. 10. The binary signal BIND eventually is delivered to a cell detecting circuit 124 comprising a shift register 120 and a cell discriminator 122. The cell detecting circuit performs cell detection.

The second embodiment is characterized in that correction processing is applied to the binary signal BIND as a preliminary stage to cell discrimination, thereby making cell discrimination easier to perform.

The correction processing involves signal compression and expansion.

Accordingly to compression, if even one item of data among those indicative of a pixel of interest and the pixels on either side thereof represents a background portion (in other words, if the corresponding pixel is indicative of background), then the item of data indicative of the pixel of interest is made "L".

The inverted binary signal BIND is compressed by a compressing circuit 102 comprising a shift register 104 and an AND circuit 106. More specifically, the shift register 104 is inputted bits $b_0$, $b_1$, $b_2$ in the order mentioned, so in the outputs of the register 104, the bit $b_2$ is the latest. An AND gate 106 takes the AND of the bits $b_2$, $b_1$, $b_0$, so that the BIND signal is compressed as indicated by a signal SHD shown in FIG. 10. A bit 304 in the signal BIND, which bit represents a dust particle as evident from FIG. 10, is compressed out of existence in the signal SHD. Thus, data representing dust particles is eliminated.

The signal SHD resulting from compression is expanded (to signal EX1D) by an expanding circuit 108 comprising a shift register 110 and an OR gate 112, and expansion is performed again (to give a signal EX2D) by an expanding circuit 114 comprising a shift register 116 and an OR gate 118.

Expansion is the opposite of compression. That is, if even one item of data of those indicative of the pixels on either side of the pixel of interest is "H" (in other words, if the corresponding pixel is indicative of a cell portion), then the date of the pixel of interest is made "H". The first expanding circuit 108 is for restoring the signal, which was compressed earlier, to its original form (though of course the data eliminated by the compressing circuit 102 is left eliminated). In case where the interior of a cell has a portion exhibiting the same brightness as the background, the second expanding circuit 114 "fills in" this portion (see signal EX2D in FIG. 10).

The signal EX2D resulting from the two expansion operations enters the shift register 120, where it is subjected to a serial-to-parallel conversion. The parallel data $b_0$–$b_7$ is delivered to the cell discriminator 122, where cell discrimination is carried out. By way of example, when a certain number of bits of data all attain the "H" level, a cell is judged to exist and a cell-detection signal CLS is produced as an output. The cell-detection signal CLS is sent to the strobe control circuit 84, where the strobe triggering signal is obtained. The circuitry described earlier in the first embodiment can be used as the strobe control circuit 84.

In the second embodiment of the invention, a counter circuit 126 for counting cells is additionally provided. If one cell-detection signal CLS is always generated with regard to one cell, then these signals need only be counted by a counter. However, since the amount of cell movement within the scanning time of the line sensor should be set to be slightly smaller than the cell diameter, a situation can arise in which two scans are performed with respect to one cell, as illustrated in FIG. 10. Accordingly, it is necessary to execute control in such a manner that even if two or more cell-detection signals are obtained with respect to the same cell, only one of these signals is adopted as a cell-count signal. For example, an arrangement can be adopted in which the initial detection signal CLS regarding a certain cell is employed as a cell-count signal CLC, and a second detection signal succeeding the first is neglected if this signal is obtained.

The control can be achieved with ease using a flip-flop. A flip-flop 130 is periodically cleared by a line synchronizing signal LSYNC from the line sensor. A flip-flop 132 is cleared by the image processor 52 whenever measurement starts. The initial state of a Q output CLL of flip-flop 130 is "L", and the initial state of a $\overline{Q}$ output CEN of flip-flop 132 is "H". The output CLL of flip-flop 130 rises from the "L" to the "H" level in response to the leading edge of the first detection signal CLS regarding a certain cell. The output CEN of the flip-flop 132 remains at the "H" level. An AND gate 134 takes the AND of the cell-detection signal CLS and the output signal CEN of flip-flop 132, and outputs the cell-count signal CLC, which enters a counter 128.

The state of signal CLL is sampled at the leading edge of the next line synchronizing signal LSYNC. In other words, if the cell-detection signal CLS has been detected in the preceding period, the signal CLL will be "H" and therefore the output CEN of flip-flop 132 will be "L". The flip-flop 130 is then cleared, and the signal CLL reverts from the "H" level to the initial "L" level. If the cell-detection signal CLS is obtained following this period, the cell-count signal CLC is not produced since the output CEN of flip-flop 132 is "L".

From this point onward, and in similar fashion, the cell-count signal CLC will not be obtained even if a cell-detection signal is obtained subsequent scanning periods. Thus, in a case where cell-detection signals are obtained in succession, a cell-count signal is obtained only with regard to the first cell-detection signal.

When a cell-detection signal has not been obtained, the output CLL of flip-flop 130 remains at the "L" level. Therefore, the output CEN of flip-flop 132 rises from "L" to "H" at the leading edge of the line synchronizing signal LSYNC of the next period. Then, when the cell-detection signal CLS is obtained, the cell-count signal CLC is outputted.

A third embodiment of the present invention will now be described. In comparison with the second embodiment of the invention, this embodiment is characterized in that the control circuit 50 is furnished with a pulse-width correcting function for accurately obtaining the size (outer diameter) of a particle such as a cell, as well as a function for creating a particle-size distribution and selecting particles based upon size.

Figure 11A:
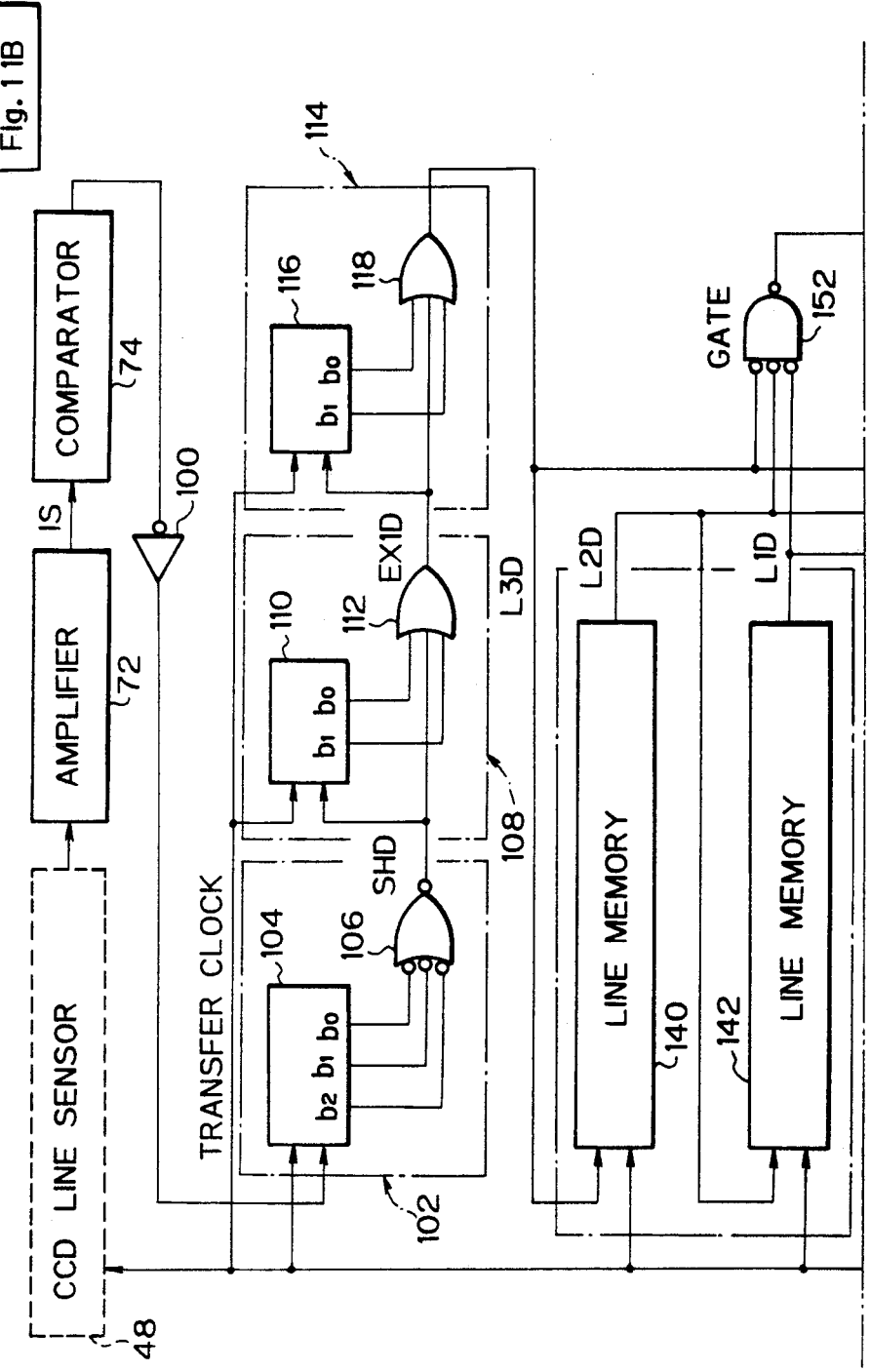
Figure 11B:
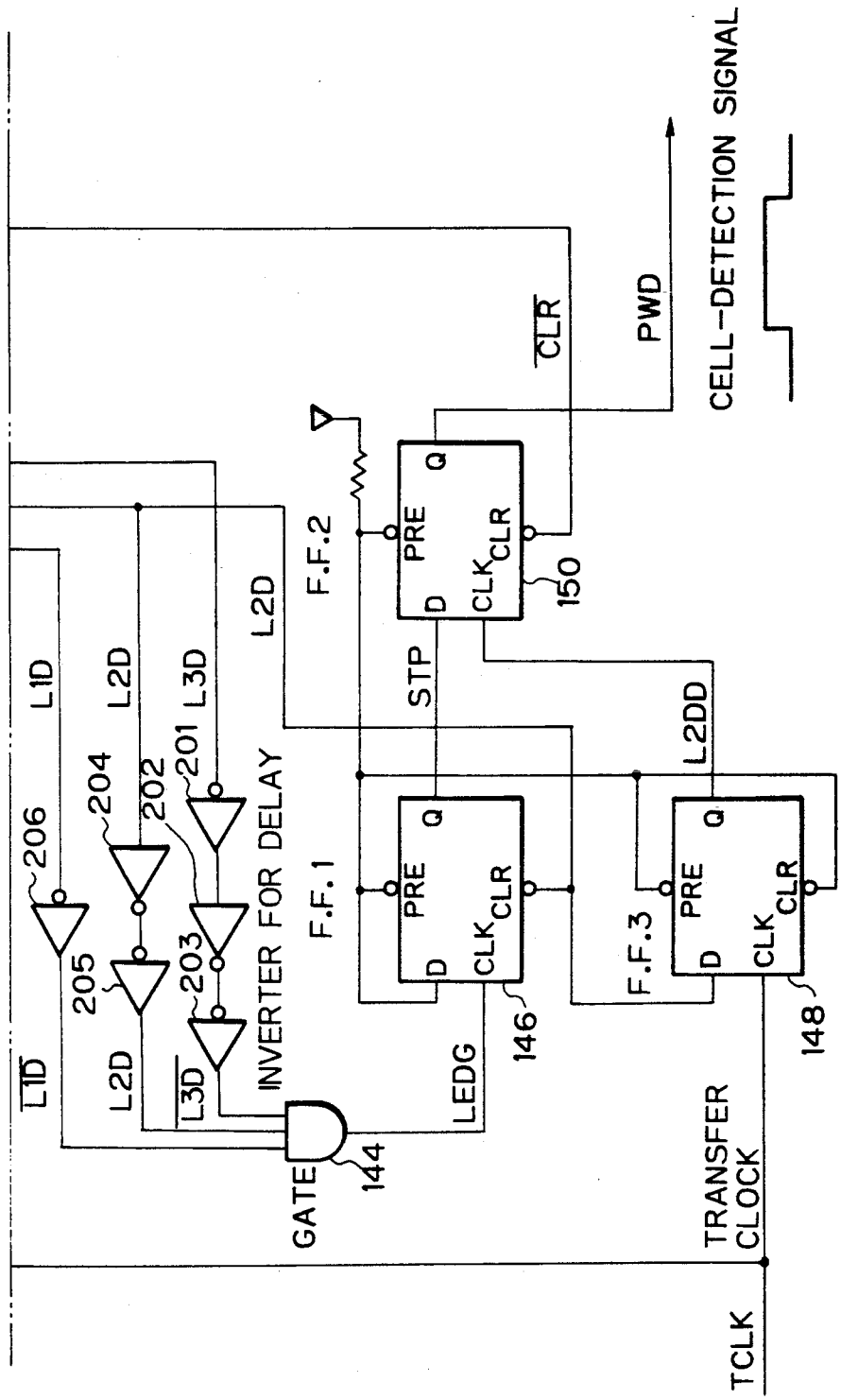
Figure 12B:
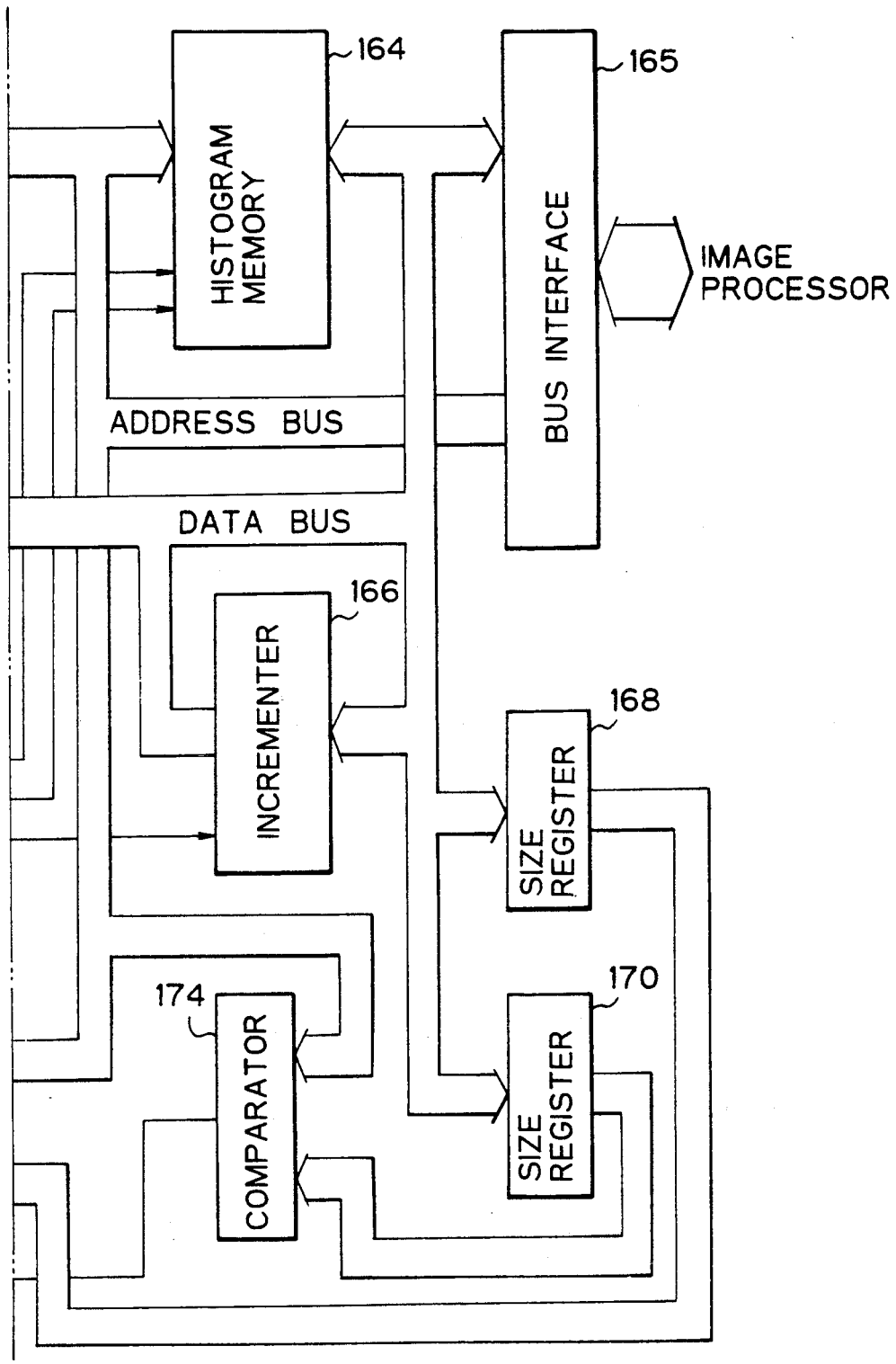
Figure 13:
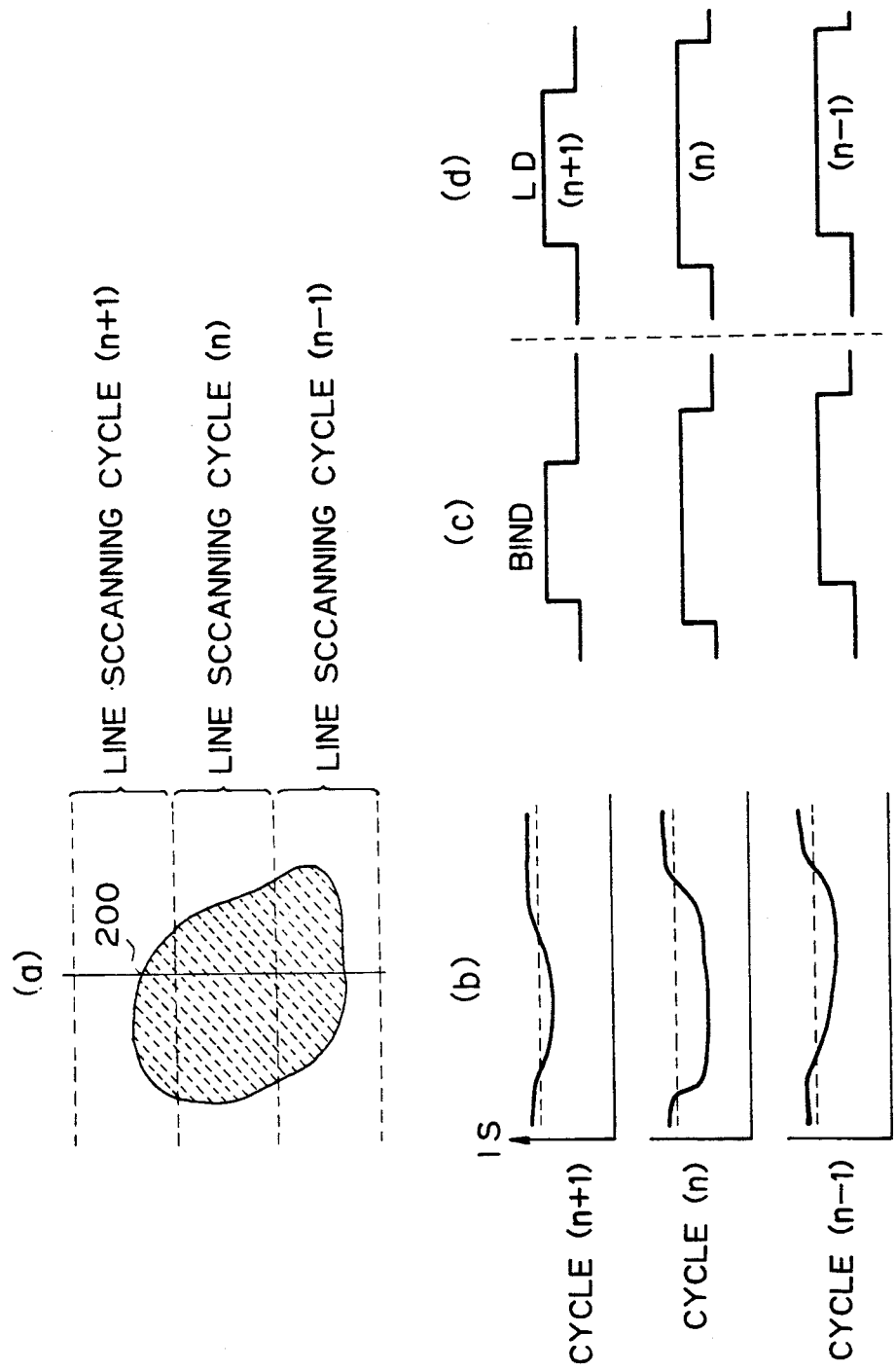
FIGS. 13 and 14 are a waveform diagram and a timing chart, respectively, for describing the operation of the circuit shown in FIG. 11.
Figure 14:
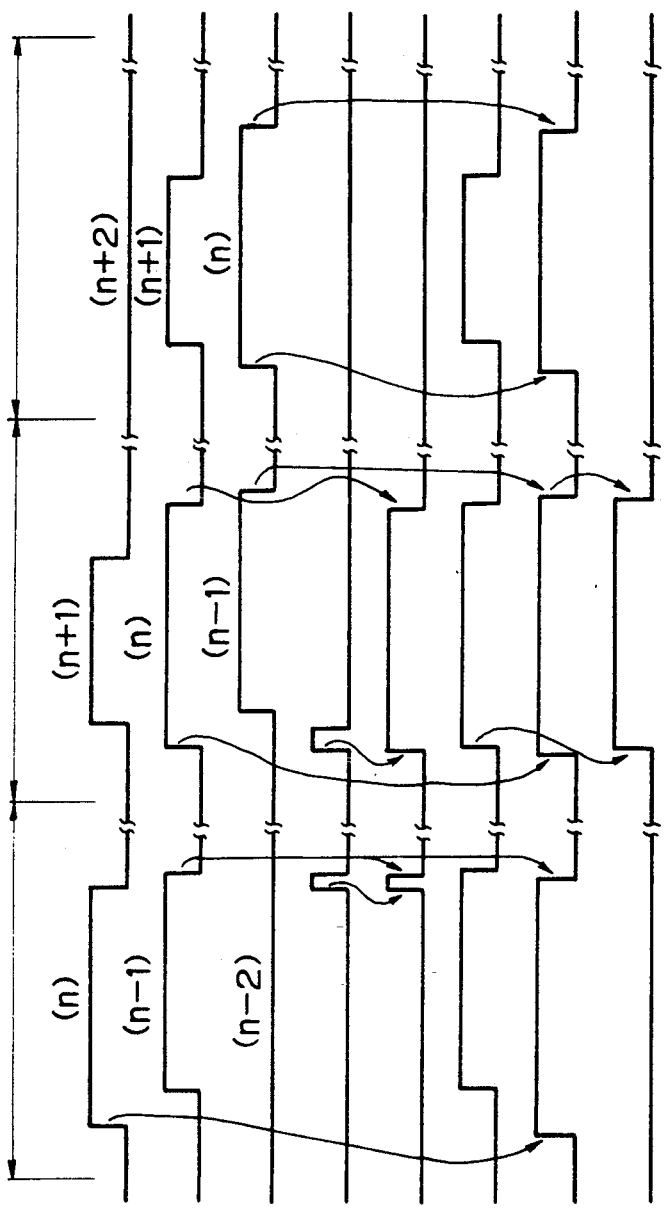
Figure 15:
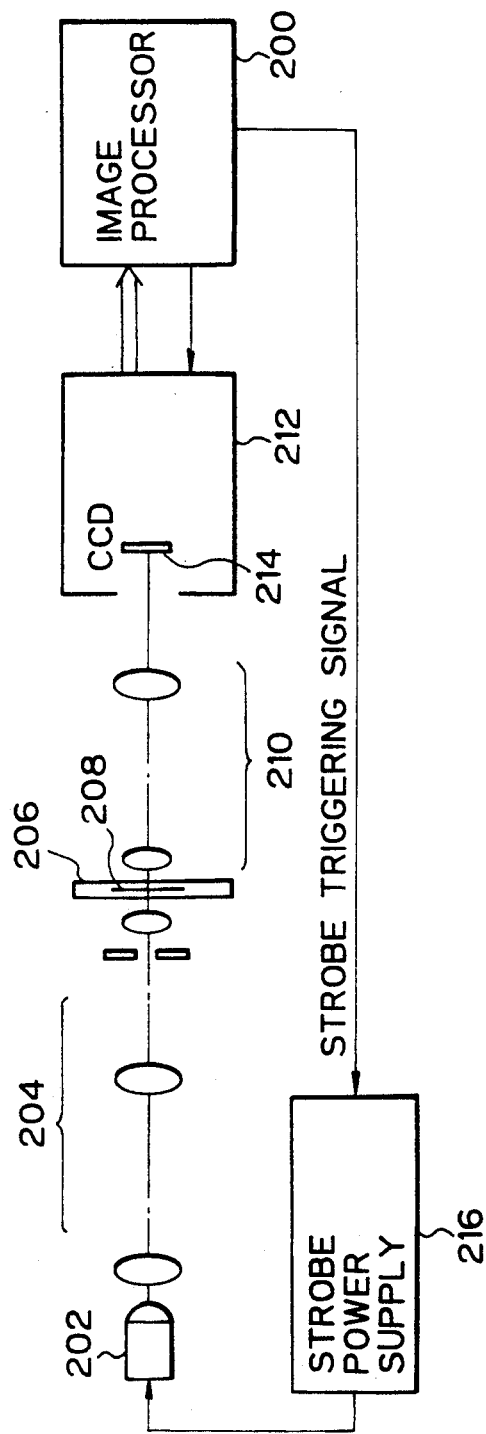
FIG. 15 is a block diagram showing the principal components of an apparatus according to the prior art.
Figure 16:
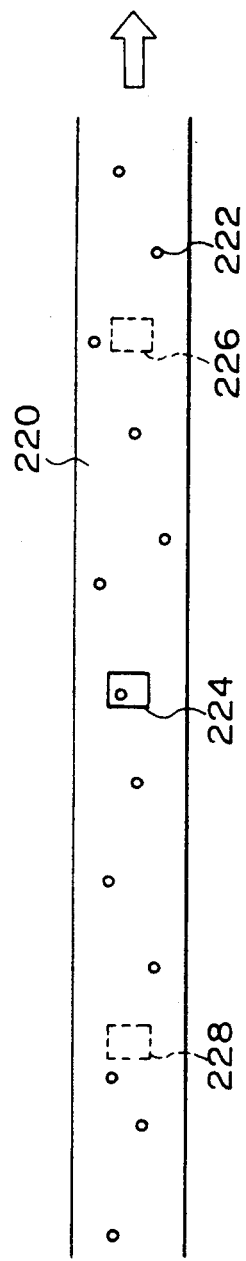
FIG. 16 is an enlarged view showing part of the flow of a sample solution as seen from the image pick-up side of the apparatus in FIG. 15.
Figure 17:
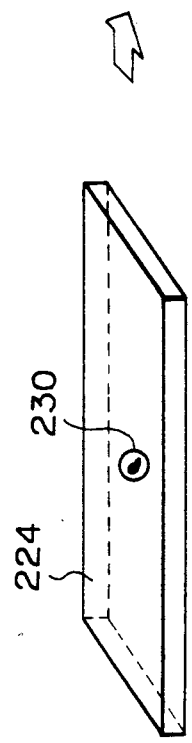
FIG. 17 is a perspective view showing an image pick-up area.

FIGS. 11 and 12 are block diagrams showing the principal components of the third embodiment of the present invention, and FIGS. 13 and 14 are a waveform diagram and timing chart, respectively, for describing the operation of the circuit shown in FIG. 11.

In FIG. 11, characters identical with those in FIG. 9 designate like or corresponding parts.

The operation of the third embodiment constructed as shown will be described for a case where scanning is performed a plurality of cycles with regard to one cell 200, as shown in FIG. 13(a). More specifically, FIG. 13(a) illustrates a case where one cell 200 passes by the line image sensor 48 in each of three line scanning cycles (n−1), (n), (n+1).

In the third embodiment, operations up to generation of the expanded signals are similar to those of the second embodiment described above. Specifically, as illustrated in FIG. 13(b), a voltage corresponding to the quantity of light accumulated pixel by pixel in one scanning period is outputted by the line image sensor 48 in synch with the transfer clock TCLK. This signal is amplified by the amplifier 72 before being binarized by the comparator 74, as shown in FIG. 13(c). The dashed line in FIG. 13(b) indicates the threshold voltage used in the comparator. The resulting binary signal is inverted by the inverter 100. The binary signal BIND outputted by the inverter 100 is compressed by the compressing circuit 102, and then expansion processing is applied by the expanding circuits 108 and 114 to obtain an expanded signal LD for a one-line scan, as shown in FIG. 13(d).

In FIG. 13(d), the expanded signal is designated by LD in order to distinguish it from that of the second embodiment shown in FIG. 10. However, LD means an expanded signal for one line of scanning. In addition, FIG. 13(d) shows only expanded signals corresponding to respective ones of the three line scanning cycles depicted in FIG. 13(a). However, in a line scanning cycle (n−2) and a line scanning cycle (n+2) (neither of which are shown) in which the cell 200 does not pass by the line image sensor 48, the sensor output attains the "H" level and the binary signal BIND assumes the "L" level, as described earlier. The expanded signal LD become an "L" level signal in each of these cases.

The second expansion performed by the expanding circuit 114 is not for filling in bright portions within the cell but rather is for obtaining a pulse width which more correctly represents the size of the cell image. That is, since the brightness of the background portion imaged on the line sensor possesses slight shading in the line-scanning direction, the threshold level must be set somewhat close to the voltage level of the cell portion upon taking the effect of this shading into account. To this end, the pulse width of the cell portion following binarization becomes less than in actuality. Accordingly, this is corrected for by the second expansion processing to obtain a binary signal having a width closer to the cell diameter. However, the expanded signal does not have a pulse width that accurately corresponds to the size of the cell.

According to the third embodiment of the invention, a pulse-width correction is performed to obtain, only once, a cell-detection signal which accurately reflects the size of a cell. This signal is obtained from binary signals of a plurality of line scans acquired by scanning one cell that has been subjected to the aforementioned expansion processing. More specifically, the third embodiment is such that when a cell is sensed by the line image sensor 48, the scanning line of interest is decided. Then, when the binary signal BIND of this scanning line of interest rises more rapidly than the binary signals BIND corresponding to the scans before and after the scanning line of interest, the OR is taken of these three binary signals BIND and the result of the OR operation is adopted as the cell-detection signal.

This will be described based upon FIGS. 11, 13 and 14.

In FIG. 14, L3D represents an expanded signal corresponding to the current one line of scanning data of the line sensor 48, L2D represents an expanded signal corresponding to one line of scanning data of the line sensor 48 one scanning period earlier, and L1D represents an expanded signal corresponding to one line of scanning data of the line sensor 48 two scanning periods earlier. Other characters in FIG. 14 indicate the signals illustrated in FIG. 11.

Under these conditions, the expanding circuit 114 outputs the expanded signal L3D. The signal L3D enters a first line memory 140, which outputs this signal as the signal L2D after one scanning period of the line image sensor 48. The signal L2D enters a second line memory 142, which outputs this signal as the signal L1D after an addition one scanning period of the line image sensor 48.

According to this method, an item of scanning data (signal L2D) of the scanning line of interest and items of scanning data (signals L3D and L1D) before and after the scanning line of interest are obtained.

The signal L3D enters an AND gate 144 via inverters 201, 202, and 203, the signal L2D enters the AND gate 144 via inverters 204, 205, and the signal L1D enters the AND gate 144 via an inverter 206. As a result, the AND gate 144 opens to deliver a signal LEDG only when the signal L2D corresponding to the scanning data of the scanning line of interest attains the "H" level.

At the leading edge of the signal LEDG, a Q output STP of a flip-flop 146 attains the "H" level. The flip-flop 146 is cleared as a result of the signal L2D of the scanning line of interest reverting to the "L" level.

As shown in FIG. 14, it should be noted that the timing signal LEDG attains the "H" level not only when the signal L2D rises the first time but also when the signal L2D decays the final time. It is necessary to distinguish between the two. The Q output STP of flip-flop 146 rises at the leading edge of the timing signal LEDG and decays when the signal L2D assumes the "L" level. Accordingly, in a case where the signal L2D rises earlier than the other signals L1D, L3D, the signal STP becomes a signal identical with the signal L2D. In other words, a major difference is brought about at the moment the signal STP rises. The cell-detection signal is obtained taking account of this difference.

The signal L2D enters a flip-flop 148, as a result of which a signal L2DD delayed by one clock is obtained. In a case where the signal L2D of the line of interest rises earlier than the signal L1D or L3D, the signal STP rises at the same time as the signal L2D, as set forth above. This is one clock earlier than signal L2DD. In other words, since the signal STP is at the "H" level at the leading edge of the signal L2DD, a cell-detection signal PWD, which is the Q output of the flip-flop 150, attains the "H" level at the leading edge of the signal L2DD. An OR gate 152 takes the OR of the signals L1D, L2D and L3D. The flip-flop 150 is cleared by a signal $\overline{CLR}$, which is the result of the OR operation, and therefore the cell-detection signal PWD reverts to the "L" level.

The reason for providing the input side of the AND gate 144 with the plurality of delaying inverters which apply different time delays to the data L1D, L2D, L3D is to prevent erroneous operation which would occur if these three strings of data were to attain the "H" level simultaneously.

It should be evident that it is permissible also to apply the trigger signal to the strobe power supply 10 in the interval during which the first image pick-up means 36 is capable of image pick-up, by actuating the strobe control circuit 84 using the cell-detection signal.

Thus, the cell-detection signal PWD representing cell size by pulse width can be obtained.

If the cell-detection signal which correctly represents cell size is used, a particle-size distribution can be created and the strobe can be controlled in such a matter that only cells within a desired range of sizes are selected and photographed by the video camera. Of course, the number of cells which pass through the image pick-up area can be calculated from a histogram, or a counter can be provided for counting the cells.

The creation of a particle-size distribution and a size selecting function will now be described with reference to the circuit diagram of FIG. 12.

The cell-detection signal PWD enters a size counter 160, which counts clock pulses for which the signal PWD is continuously at the "H" level. When the signal PWD reverts to the "L" level and counting ends, the value recorded in the counter 160 is latched in an address register 162 and supplied to the address line of a histogram memory 164. Frequency data stored at a designated address is read out of the histogram memory 164. The read frequency data is incremented by one by an incrementer 166, and the incremented frequency data is written in the memory 164 again.

The reason for providing the address register 162 is to make sure that even if two cell-detection signals PWD are close together, the latter will be processed without being overlooked. In other words, delivering the value in size counter 160 to the address register 162 makes it possible to promptly count cell sizes of closely arriving cell-detection signals.

Control for selectively picking up the images solely of cells whose sizes are within a certain range will now be described. To make this control possible, it is required that upper- and lower-limit values of cell size be set in advance. The desired upper- and lower-limit values are set in respective size registers 168, 170. The cell-size value that has been set in the address register 162 is compared with the upper- and lower-limit values by means of comparators 172, 174, respectively. If the cell size is within the set range and there is an output from a control circuit 163, the trigger signal for causing a strobe-light emission is outputted via an AND gate 176. The control circuit 163 includes control circuitry similar to that of the strobe control circuit 84 described in connection with FIG. 6.

If the upper-limit value is set to be large enough, cells in excess of a certain size can be selected. If the lower-limit value is set to be small enough, cells below a certain size can be selected.

Selecting cells to be imaged based upon size is very useful in cases where the particles contained in a sample solution are of a very wide variety.

In addition, the cell-detection signals PWD are counted one after another by a counter 161 for cell-counting purposes, thus making it possible to accurately count the number of cells which pass through the image pick-up area.

The control circuit 163 in FIG. 12 is for controlling the operations described above. The arrangement of FIG. 12 further includes a bus interface 165 for interfacing the image processor 52.

The advantages of the present invention will now be described.

According to the present invention, a particle image analyzer is provided with a second light source, second image pick-up means and a control circuit and is so adapted as to take a still picture of a particle when the particle has arrived at the image pick-up area. Accordingly, even a sample having a low particle content can have cells of interest photographed at a much higher probability. As a result, the analytical precision and the processing capability of the apparatus are improved.

In addition, a second image pick-up zone for particle detection is linear and is formed so as to cross a first image pick-up zone that is two-dimensional. Accordingly, the positions at which cells appear in an imaged frame are limited. This means that it is unnecessary to process the entire frame at the time of image processing, for it will suffice to process only a limited area. The result is simplified processing and higher processing speed.

There is not much of a decline in image pick-up probability even though the volume of the first image pick-up zone is made small. This can be utilized to reduce the surface area of image pick-up, namely to raise magnification and obtain a larger cell image in relative terms. In addition, the thickness of the sample-solution flow can be made small to obtain a better focused image. This in turn makes possible more reliable image processing and analysis.

Further, since the particle image analyzer of the invention is additionally provided with compressing and expanding circuits, corrective processing such as noise removal and fill-in can be executed so that particle detection can be carried out more accurately.

Furthermore, the arrangement of the invention is such that when one particle is scanned a plurality of times by the second image pick-up means, scanning data of the scanning line of interest and scanning data representing the scanning lines before and after the scanning line of interest are extracted together by using line memories, the OR is taken of these plural items of scanning data when the scanning data representing the scanning line of interest rises the first time, and a particle-detection signal is formed based on the result of the OR operation. This makes it possible to obtain a particle-detection signal in which the size of one particle is accurately represented by pulse width one time only.

In addition, the apparatus of the invention is so adapted that one particle-count signal is obtained for one particle, and the particle-count signal is counted by a counter. As a result, a count of particles which pass through the image pick-up area can be obtained.

Further, pulse widths of particle-detection signals can be stored in a histogram memory successively via a size counter. Accordingly, a histogram relating to pulse width can be obtained. If such a histogram is utilized, new information, such as the distribution of particle sizes, can be acquired.

Further, it is so arranged that data representing the pulse width of a particle-detection signal obtained by the size counter is compared with data indicative of upper- and lower-limit values stored in a size register. This makes it possible to obtain particle-detection signals whose pulse widths fall within a range between the upper- and lower-limit values, and thus only those particles whose sizes are within a specific range can be photographed selectively. In cases where the sample solution contains a wide variety of particle components having different sizes, this feature of the invention is particularly useful because it allows particles solely of a desired size to be made the object of analysis.

As many apparently widely different embodiments of the present invention can be made without departing from the spirit and scope thereof, it is to be understood that the invention is not limited to the specific embodiments thereof except as defined in the appended claims.

What is claimed is:

1. A particle image analyzing apparatus comprising:
   a flow cell formed to have a flat flow path for forming a sample solution containing particle components to be detected into a flat flow,
   a visible light source arranged on a first side of said flow cell for irradiating the sample solution flowing through said flow cell with strobe light,
   first image pick-up means having a two-dimensional image pick-up zone on the flow of the sample solution and being arranged on a second side of said flow cell for taking a still picture of the particle components in the sample solution irradiated by said visible light source, and
   processing means for executing desired analytical processing based on image data from said first image pick-up means,
   said particle image analyzing apparatus being characterized by further comprising:
   a non-visible light source arranged on the first side of said flow cell for irradiating the sample solution in said flow cell at all times;
   second image pick-up means having a linear image pick-up zone formed so as to cross the flow direction of the sample solution within the image pick-up area of said first image pick-up means on the flow of the sample solution said second image pick-up means being arranged on the second side of said flow cell for picking up an image of the sample solution in said flow cell irradiated by said non-visible light source;
   control means for detecting, based on image pick-up data from said second image pick-up means, whether a particle component to be detected is present in an image pick-up zone of said first image pick-up means, and flashing, based on detection of the particle component, said first light source in a predetermined image pick-up interval of said first image pick-up means; and
   light-selecting means for selecting light from said visible light source and light from said non-visible light source in such a manner that only visible light is applied to said first image pick-up means and only non-visible light is applied to said second image pick-up means.

2. The apparatus according to claim 1, wherein a cylindrical lens is provided between said non-visible light source and said flow cell.

3. The apparatus according to claim 1, wherein the sample solution is blood that has been subjected to hemolytic and staining treatments, and the particle components to be detected are leukocytes.

4. The apparatus according to claim 1, wherein the sample solution is urine that has been subjected to a staining treatment, and the particle components to be detected are material components contained in urine.

5. A particle imaging analyzing apparatus comprising:
   a flow cell formed to have a flat flow path for forming a sample solution containing particle components to be detected into a flat flow,
   a first light source arranged on a first side of said flow cell for irradiating the sample solution flowing through said flow cell with strobe light,
   first image pick-up means arranged on a second side of said flow cell for taking a still picture of the particle components in the sample solution irradiated by said first light source, and processing means for executing desired analytical processing based on image data from said first image pick-up means, said particle image analyzing apparatus being characterized by further comprising:

a second light source arranged on the first side of said flow cell for irradiating the sample solution in said flow cell at all times;

second image pick-up means arranged on the second side of said flow cell and having linearly arrayed image pick-up elements for picking up an image of the sample solution in said flow cell irradiated by said second light source;

first means for comparing data of each pixel in one scanning line of an image, which data is sequentially outputted by said second image pick-up means, with a predetermined reference level, and outputting a discrimination signal with indicates whether the pixel data is that of a particle component or non-particle component;

particle detecting means for outputting particle-detection signal in a case where an output from said first means is indicative of a particle component successively a predetermined number of times;

second means for outputting a signal, which flashes said first light source, when the particle-detection signal is outputted in an interval in which said first image pick-up is capable of image pick-up;

a compressing circuit which is connected to said first means and holds three pixel portions of the discrimination signal from said first means, said compressing circuit outputting, as a discrimination signal indicative of a pixel midway between the other two pixels, a discrimination signal indicative of a detected particle component in a case where all three pixel portions of the discrimination signal represent the particle component, and a discrimination signal indicative of a non-particle component in all other cases;

a first expanding circuit connected to said compressing circuit for outputting, as a discrimination signal indicative of a pixel midway between the other two pixels, a discrimination signal indicative of a particle component in a case where at least one output among three successive outputs from said compressing circuit is a discrimination signal indicative of a particle component; and a second expanding circuit connected to said first expanding circuit for outputting, as a discrimination signal indicative of a pixel midway between the other two pixels, a discrimination signal indicative of a particle component in a case where at least one output among three successive outputs from said first expanding circuit is a discrimination signal indicative of a particle component.

6. A particle image anaylzing apparatus comprising:

a flow cell formed to have a flat flow path for forming sample solution containing particle components to be detected into a flat flow, a visible light source arranged on a first side of said flow cell for irradiating the sample solution flowing through said flow cell with strobe light, first image pick-up means having a two-dimensional image pick-up zone on the flow of the sample solution and being arranged on a second side of said flow cell for taking a still picture of the particle components in the sample solution irradiated by said visible light source, and processing means for executing desired analytical processing based on image data from said first image pick-up means, said particle image analyzing apparatus being characterized by further comprising:

a second non-visible light source arranged on the first side of said flow cell for irradiating the sample solution in said flow cell at all times;

second image pick-up means having a linear image pick-up zone on the flow of the sample solution formed so as to cross the flow direction of the sample solution within the image pick-up area of said first image pick-up means, the image pick-up zone of said second image pick-up means being formed within the image pick-up zone of said first image pick-up means said second image pick-up means being arranged on the second side of said flow cell and having linearly arrayed image pick-up elements for picking up an image of the sample solution in said flow cell irradiated by said non-visible light source;

first means for comparing data of each pixel in one scanning line of an image, which data is sequentially outputted by said second image pick-up means, with a predetermined reference level, and outputting a discrimination signal which indicates whether the pixel data is that of a particle component or non-particle component;

particle detecting means for outputting particle-detection signal in a case where an output from said first means is indicative of a particle component successively a predetermined number of times;

second means for outputting a signal, which flashes said visible light source, when the particle-detection signal is outputted in an interval in which said first image pick-up is capable of image pick up; and light-selecting means for selecting light from said visible light source and light from said non-visible light source in such a manner that only visible light is applied to said first image pick-up means and only non-visible light is applied to said second image pick-up means.

7. The apparatus according to claim 6, wherein a cylindrical lens is provided between said non-visible light source and said flow cell.

8. The apparatus according to claim 6, wherein the sample solution is blood that has been subjected to hemolytic and staining treatments, and the particle components to be detected are leukocytes.

9. The apparatus according to claim 6, wherein the sample solution is urine that has been subjected to a staining treatment, and the particle components to be detected are material components contained in urine.

10. The apparatus according to claim 6, further comprising:

a compressing circuit which is connected to said first means and holds three pixel portions of the discrimination signal from said first means, said compressing circuit outputting, as a discrimination signal indicative of a pixel midway between the other two pixels, a discrimination signal indicative of a detected particle component in a case where all three pixel portions of the discrimination signal represent the particle component, and a discrimination signal indicative of a non-particle component in all other cases;

a first expanding circuit connected to said compressing circuit for outputting, as a discrimination signal indicative of a pixel midway between the other two pixels, a discrimination signal indicative of a particle component in a case where at least one output among three successive outputs from said compressing circuit is a discrimination signal indicative of a particle component; and a second expanding circuit connected to said first expanding circuit for outputting, as a discrimination signal indicative of a pixel midway between the other two pixels, a discrimination signal indicative of a particle component in a case where at least one output among three successive outputs from said first expanding circuit is a discrimination signal indicative of a particle component.

11. The apparatus according to claim 6, 10 or 5 further comprising a particle counting circuit which includes:

a circuit which, in a case where the particle-detection signal is outputted successively in a plurality of image pick-up periods of said second image pick-up means, outputs, as a particle-count signal, solely a particle-detection signal inputted in an initial image pick-up period of said plurality of image pick-up period; and a counting circuit for counting the particle-count signal.

12. A particle image analyzing apparatus comprising:

a flow cell formed to have a flat flow path for forming a sample solution containing particle components to be detected into a flat flow, a first light source arranged on a first side of said flow cell for irradiating the sample solution flowing through said flow cell with strobe light, first image pick-up means arranged on a second side of said flow cell for taking a still picture of the particle components in the sample solution irradiated by said first light source, and processing means for executing desired analytical processing based on image data from said first image pick-up means, said particle image analyzing apparatus being characterized by further comprising:

a second light source arranged on the first side of said flow cell for irradiating the sample solution in said flow cell at all times;

second image pick-up means arranged on the second side of said flow cell and having linearly arrayed image pick-up elements for picking up an image of the sample solution in said flow cell irradiated by said second light source;

first means for comparing data of each pixel in one scanning line of an image, which data is sequentially outputted by said second image pick-up means, with a predetermined reference level, and outputting a discrimination signal which indicates whether the pixel data is that of a particle component or non-particle component;

a compressing circuit which is connected to said first means and holds three pixel portions of the discrimination signal from said first means, said compressing circuit outputting, as a discrimination signal indicative of a pixel midway between the other two pixels, a discrimination signal indicative of a detected particle component in a case where all three pixel portions of the discrimination signal represent the particle component, and a discrimination signal indicative of a non-particle component in all other cases;

a first expanding circuit connected to said compressing circuit for outputting, as a discrimination signal indicative of a pixel midway between the other two pixels, a discrimination signal indicative of a particle component in a case where at least one output among three successive outputs from said compressing circuit is a discrimination signal indicative of a particle component;

a second expanding circuit connected to said first expanding circuit for outputting, as a discrimination signal indicative of a pixel midway between the other two pixels, a discrimination signal indicative of a particle component in a case where at least one output among three successive outputs from said first expanding circuit is a discrimination signal indicative of a particle component;

second means for obtaining a pixel discrimination signal line by line of three neighboring scanning lines in response to an output from said second expanding circuit, third means which, in a case where the pixel discrimination signal, from said second means, of a central scanning line among said three scanning lines indicates earliest the particle component, is for generating a particle-detection signal at the moment said particle component is indicated, and ends generation of the particle-detection signal at the moment all three scanning lines of the pixel discrimination signal indicate a non-particle component; and fourth means for outputting a trigger signal which flashes said first light source when the particle-detection signal is outputted in an interval in which said first image pick-up means is capable of image pick-up.

13. The apparatus according to claim 12, further comprising:

a counter for measuring pulse width of the particle-detection signal; and a histogram memory connected to said counter, wherein whenever a pulse width is measured, said histogram memory stores the frequency thereof.

14. A particle image analyzing apparatus according to claim 12 or 13, further comprising:

a size counter for measuring the pulse width of the particle-detection signal;

a first size register for storing an upper-limit value of the pulse width;

a second size register for storing a lower-limit value of the pulse width;

a first comparator to which the upper-limit value is inputted as reference data and the pulse width from said size counter is inputted as data to be judged;

a second comparator to which the lower-limit value is inputted as reference data and the pulse width from said size counter is inputted as data to be judged;

a control circuit for generating a control signal which indicates the interval in which said first image pick-up means is capable of image pick-up; and means for outputting the trigger signal which flashes said first light source when there are outputs from said first and second comparators which indicate that the pulse width is within a set range and an output from said control circuit.

15. The apparatus according to claim 12, wherein said first image pick-up means has a two-dimensional image pick-up zone on the flow of the sample solution, and said second image pick-up means has a linear image pick-up zone on the flow of the sample solution, the image pick-up zone of said second image pick-up means being formed within the image pick-up zone of said first image pick-up means.

16. The apparatus according to claim 12 or 15, wherein the image pick-up zone of said second image pick-up means is formed so as to cross the flow direction of the sample solution within the image pick-up area of said first image pick-up means.

17. The apparatus according to claim 12, wherein light emitted by said first light source is visible light, and light emitted by said second light source in non-visible light.

18. The apparatus according to claim 12, further comprising light-selecting means for selecting light from said first light source and light from said second light source in such a manner that only visible light is applied to said first image pick-up means and only non-visible light is applied to said second image pick-up means.

19. The apparatus according to claim 12, wherein a cylindrical lens is provided between said second light source and said flow cell.

20. The apparatus according to claim 12, wherein the sample solution is blood that has been subjected to hemolytic and staining treatments, and the particle components to be detected are leukocytes.

21. The apparatus according to claim 12, wherein the sample solution is uring that has been subjected to a staining treatment, and the particle components to be detected are material components contained in urine.

* * * * *

UNITED STATES PATENT AND TRADEMARK OFFICE
CERTIFICATE OF CORRECTION

PATENT NO. : 5,159,642

DATED : October 27, 1992

INVENTOR(S) : Tokihiro Kosaka

It is certified that error appears in the above-identified patent and that said Letters Patent is hereby corrected as shown below:

Column 7, line 65, delete "sheated" and insert --sheathed--.

Column 11, delete the equation at line 19 beginning "$\overline{CLR}=$"

and insert $--\overline{CLR}=$  --.

Signed and Sealed this

Sixteenth Day of November, 1993

*Attest:*

BRUCE LEHMAN

*Attesting Officer*   *Commissioner of Patents and Trademarks*